(12) United States Patent
Hepner

(10) Patent No.: US 12,246,028 B2
(45) Date of Patent: *Mar. 11, 2025

(54) USE OF DANTROLENE AND DANTROLENE PRODRUGS TO TREAT RADIATION EXPOSURE

(71) Applicant: EAGLE RESEARCH LABS LIMITED, Qormi (MT)

(72) Inventor: Adrian Hepner, Woodcliff Lake, NJ (US)

(73) Assignee: EAGLE RESEARCH LABS LIMITED, Qormi (MT)

( * ) Notice: Subject to any disclaimer, the term of this patent is extended or adjusted under 35 U.S.C. 154(b) by 771 days.

This patent is subject to a terminal disclaimer.

(21) Appl. No.: 17/295,522

(22) PCT Filed: Nov. 27, 2019

(86) PCT No.: PCT/US2019/063503
§ 371 (c)(1),
(2) Date: May 20, 2021

(87) PCT Pub. No.: WO2020/112932
PCT Pub. Date: Jun. 4, 2020

(65) Prior Publication Data
US 2022/0023319 A1 Jan. 27, 2022

Related U.S. Application Data

(60) Provisional application No. 62/772,001, filed on Nov. 27, 2018.

(51) Int. Cl.
A61K 31/675 (2006.01)
A61K 9/00 (2006.01)
A61K 31/4178 (2006.01)
A61P 39/00 (2006.01)

(52) U.S. Cl.
CPC .......... *A61K 31/675* (2013.01); *A61K 9/0019* (2013.01); *A61K 31/4178* (2013.01); *A61P 39/00* (2018.01)

(58) Field of Classification Search
CPC ............... A61K 31/675; A61K 9/0019; A61K 31/4178; A61P 39/00
See application file for complete search history.

(56) References Cited

U.S. PATENT DOCUMENTS

| 4,163,058 A | 7/1979 | Stella et al. |
| 11,352,347 B2* | 6/2022 | Wescott ............... A61K 9/0043 |
| 2009/0093531 A1 | 4/2009 | Malkawi |
| 2015/0231093 A1* | 8/2015 | Miller ............... A61K 31/145 514/665 |
| 2020/0239455 A1* | 7/2020 | Wescott ............... C07D 405/12 |
| 2022/0324850 A1* | 10/2022 | Wescott ............... C07F 9/65586 |

FOREIGN PATENT DOCUMENTS

| EP | 0693481 A1 | 1/1996 |
| JP | H08-183777 A | 7/1996 |
| JP | 2011-500570 A | 1/2011 |
| WO | WO-2019079721 A1 * | 4/2019 ......... A61K 31/4178 |

OTHER PUBLICATIONS

Emin Büyükokuroğlu, Mehmet, et al. Cell Biochem Funct. Jun. 2003;21(2):127-31. (Year: 2003).*
I Garau, Miquel Macià, et al. Rep. Pract. Oncol Radiother. Jul. 2011;16(4):123-30. (Year: 2011).*
Ryanodex® (dantrolene sodium) for injectable suspension, for intravenous use; Dailymed; Ref. ID: 3597641; Nat'l Library of Medicine; Jul. 2014; p. 2-11.
Yamashita Hisao; "emission of light radiation radiation damage"; Radioisotopes; Japan Isotope Association Radioisotopes; vol. 13 No. 3; May 1964; p. 244-260 (*contains English Translation*).
Varia et al.; "Phenytoin Prodrugs III: Water-Soluble Prodrugs for Oral and/or Parenteral Use"; Journal of Pharmaceutical Sciences; vol. 73 No. 8; Aug. 1984; p. 1068-1073.
Bundgaard et al.; "Pro-Drugs as Drug Delivery Systems VIII. Bioreversible Derivatization of Hydantoins by N-Hydroxymethylation"; Int'l Journal of Pharmaceutics; vol. 5; 1980; p. 67-77.
Russia Patent Application No. 2021117883; Office Action; dated Apr. 18, 2023; 17 pages.
Harkevich D. A. Farmakologia [Pharmacology], Moscow, "Medicina", 1987, pp. 47-48.
Belikov V. G. Farmacevtičeskaâ himiâ [Pharmaceutical Chemistry], textbook, 4th ed., Moscow, "MEDpress-inform", 2007, p. 622 and pp. 27-29.
Maškovskij M. D. Lekarstvennye sredstva [Drugs], vol. 1, Moscow, "Medicina", 1993, p. 8.
Maškovskij M. D. Lekarstvennye sredstva [Drugs], 14th ed., vol. 1, Moscow, "Medicina", 2002, pp. 8-9.
Žulenko V. N., Gorškov G. I. Farmakologiâ [Pharmacology], Moscow, KolosS, 2008, pp. 34-35.
Pharmaceutical Technology: Technology of dosage forms: Textbook for students of higher education institutions], 2nd ed., Moscow, Publishing Center "Akademiâ", 2006, p. 6.
Daniela Jornada et al., "The Prodrug Approach: A successful tool for improving drug solubility", Molecules, Dec. 29, 2015, vol. 21, No. 1, p. 42.
Mehmet Emin Buyukokuroglu et al., "Dantrolene protects erythrocytes against oxidative stress during whole-body irradiation in rats, Radioprotive Effect of Dantrolene", Cell Biochemistry and Function, Jun. 1, 2003, vol. 21, No. 2. pp. 127-131.

* cited by examiner

*Primary Examiner* — Matthew P Coughlin
*Assistant Examiner* — Quincy McKoy
(74) *Attorney, Agent, or Firm* — BakerHostetler

(57) ABSTRACT

The disclosure is directed to methods of using dantrolene, dantrolene prodrugs, or pharmaceutically acceptable salts thereof, to treat radiation exposure.

37 Claims, 11 Drawing Sheets

1: Control
2: Ryanodex pre-irradiation
3: Ryanodex post-irradiation single dose
4: Ryanodex post-irradiation multiple dose (days 1-5)

1: Control
2: Ryanodex pre-irradiation
3: Ryanodex post-irradiation single dose
4: Ryanodex post-irradiation multiple dose (days 1-5)

USE OF DANTROLENE AND DANTROLENE PRODRUGS TO TREAT RADIATION EXPOSURE

CROSS-REFERENCE TO RELATED APPLICATIONS

This application is a National Stage Application filed under 35 U.S.C. 371 of International Application No. PCT/US2019/063503, filed Nov. 27, 2019, which claims the benefit of U.S. Provisional Application No. 62/772,001, filed Nov. 27, 2018, the entirety of which is incorporated by reference herein.

TECHNICAL FIELD

The disclosure is directed to methods of using dantrolene, dantrolene prodrugs, or pharmaceutically acceptable salts thereof, to treat radiation exposure.

BACKGROUND

Acute Radiation Syndrome (ARS), also known as radiation toxicity or radiation sickness, is an acute medical condition caused by irradiation of the whole body (or a significant portion of the body), by a high dose of penetrating radiation in a short period of time, generally minutes. The leading cause of ARS is depletion of pluripotent cells in specific tissues. ARS generally follows a predictable clinical course and is characterized by signs and symptoms that are manifestations of cellular deficiencies and the reactions of various tissues and organs to ionizing radiation. High-dose ionizing radiation exposures to the whole or substantial parts of the body often result in life-threatening injuries, primarily to those radiosensitive, self-renewing tissues, but most markedly to the hematopoietic systems. The survival rate of patients with the hematopoietic syndrome decreases with increasing radiation exposure. The primary cause of death is the destruction of the bone marrow, resulting in infection and hemorrhage.

Methods of treating radiation exposure are needed.

SUMMARY

The disclosure is directed to methods of treating a subject that has been or will be exposed to radiation comprising administering to the subject a pharmaceutical composition comprising a therapeutically effective amount of dantrolene or a pharmaceutically acceptable salt thereof.

The disclosure is also directed to methods of treating a subject that has been or will be exposed to radiation comprising administering to the subject a pharmaceutical composition comprising a therapeutically effective amount of a compound of formula I

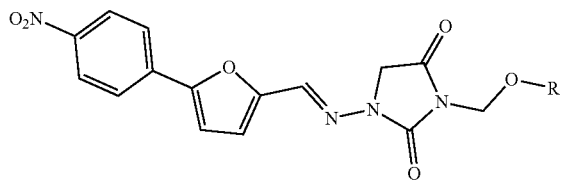

I wherein R is —P(O)(OH)$_2$ or —P(O)(OR$_1$)(OR$_2$); R$_1$ is H, —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl; and R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl; or a pharmaceutically acceptable salt thereof.

The disclosure is also directed to methods of treating a subject that has been or will be exposed to radiation comprising administering to the subject a pharmaceutical composition comprising a therapeutically effective amount of a compound of formula II

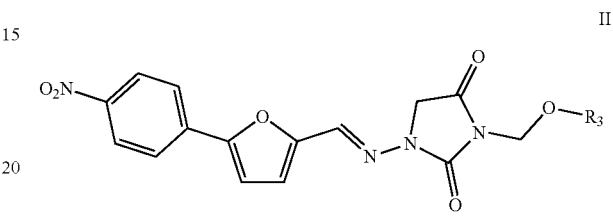

II wherein R$_3$ is H, —C(O)—Z—N(R$_4$)(R$_5$), —C(O)Z—C(O)—OH, or —C(O)—NH—Y—CH$_2$—OC(O)—Z—C(O)—OH; Z is C$_{1-6}$alk; Y is arylene; C$_{1-6}$alkyl; R$_5$ is H or C$_{1-6}$alkyl; or R$_4$ and R$_5$, together with the nitrogen to which they are attached, form a heterocycloalkyl; as well as pharmaceutically acceptable salts thereof.

The disclosure is also directed to methods of treating a subject that has been or will be exposed to radiation comprising administering to the subject a pharmaceutical composition comprising a therapeutically effective amount of a combination of any of dantrolene, a compound of formula I, a compound of formula II, or a pharmaceutically acceptable salt thereof.

BRIEF DESCRIPTION OF THE DRAWINGS

The summary, as well as the following detailed description, is further understood when read in conjunction with the appended drawings. For the purpose of illustrating the disclosed devices, systems, and methods, there are shown in the drawings exemplary embodiments of the devices, systems, and methods; however, the devices, systems, and methods are not limited to the specific embodiments disclosed. In the drawings:

FIG. 8A: Overall body weight change. FIG. 8B: Body weight change for Subset A. FIG. 8C: Body weight change for Subset B. Groups 1: Control; 2: Ryanodex pre-irradiation; 3: Ryanodex post-irradiation single dose; and 4: Ryanodex post-irradiation multiple dose (days 1-5).

FIG. 9A: Overall average mortality scores. FIG. 9B: Average mortality scores for Subset A. FIG. 9C: Average mortality scores for Subset B.

DETAILED DESCRIPTION OF ILLUSTRATIVE EMBODIMENTS

Figure 1:
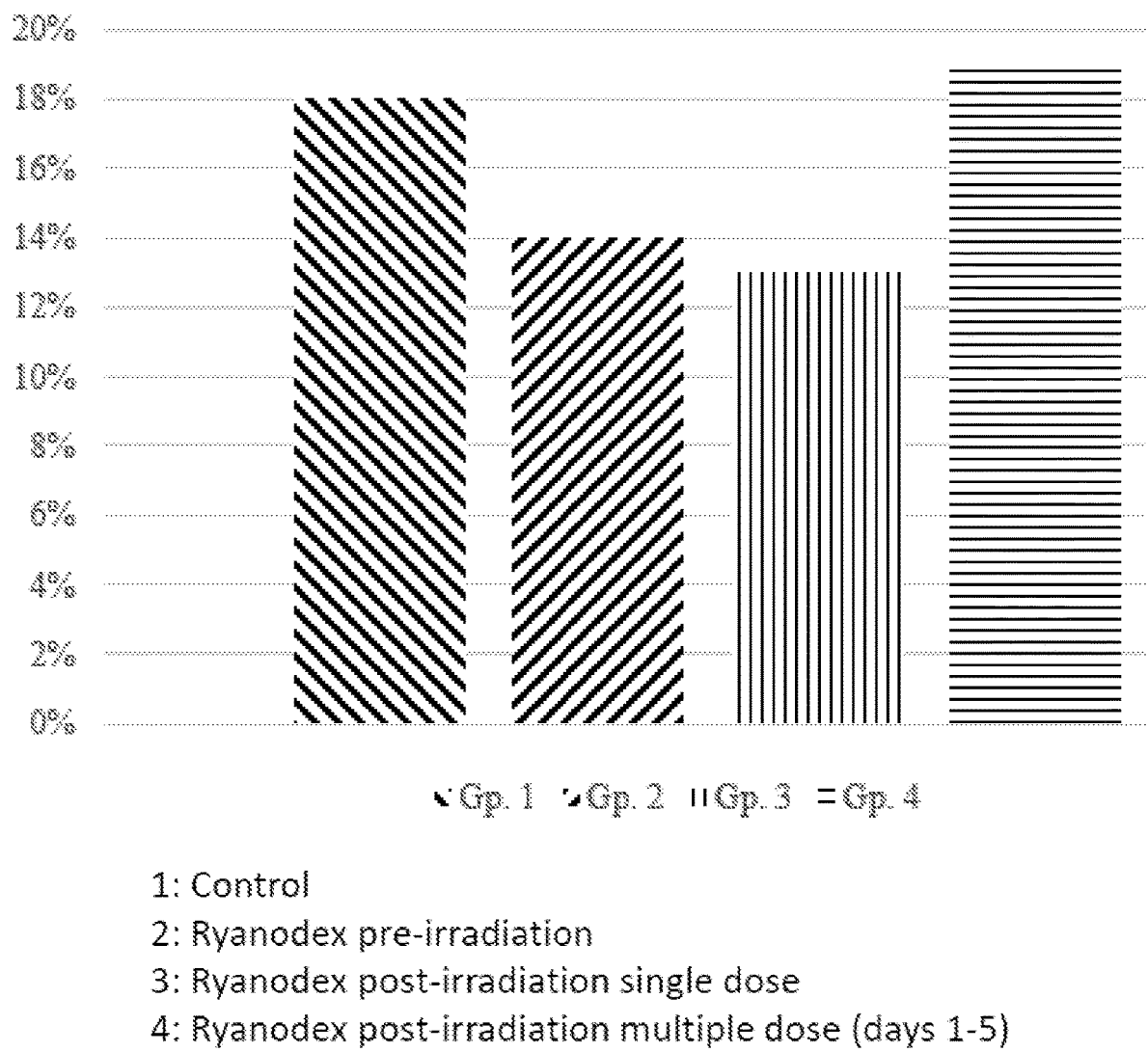
FIG. 1 is a histogram depicting the percent change in red blood cells (RBCs) between day 7 and day 30 in Ryanodex-treated animals, groups 1-4. Groups 1: Control; 2: Ryanodex pre-irradiation; 3: Ryanodex post-irradiation single dose; and 4: Ryanodex post-irradiation multiple dose (days 1-5).
Figure 2:
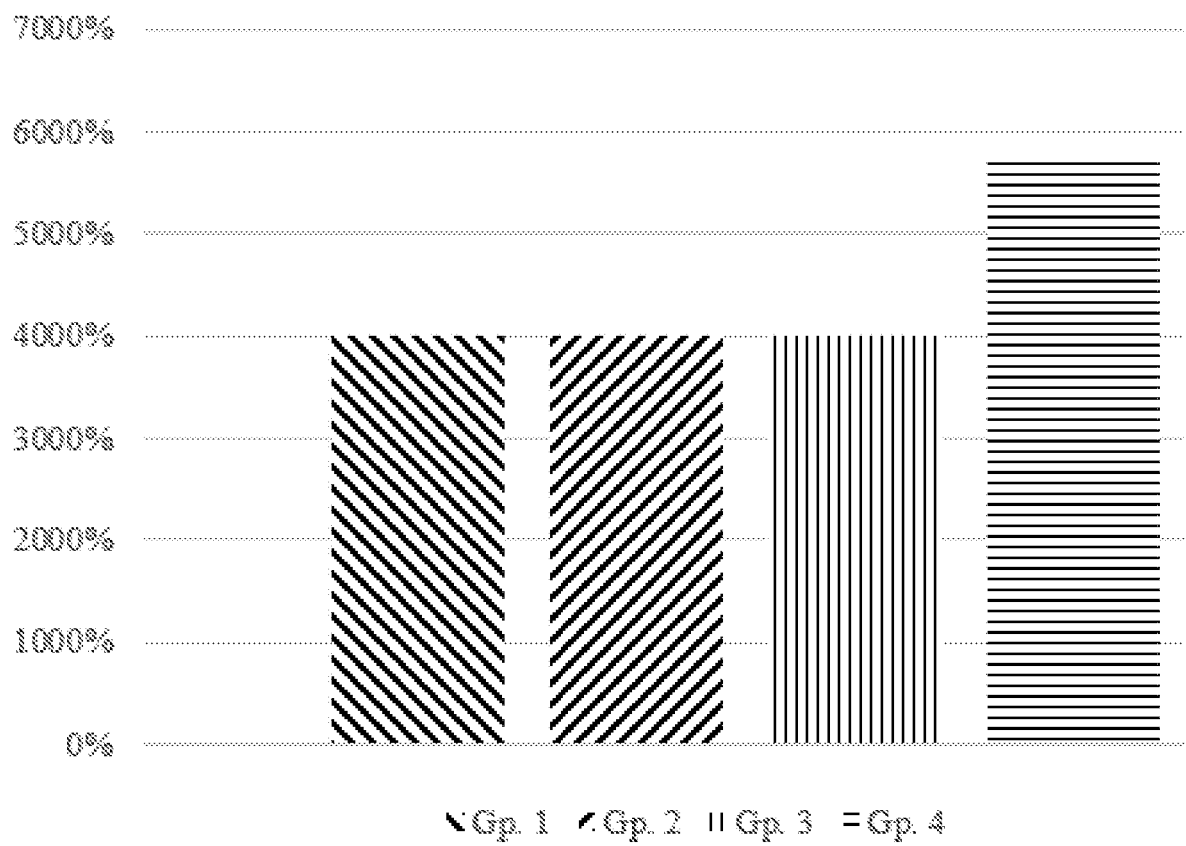
FIG. 2 is a histogram depicting the percent change in white blood cells (WBCs) between day 7 and day 30 in Ryanodex-treated animals, groups 1-4. Groups 1: Control; 2: Ryanodex pre-irradiation; 3: Ryanodex post-irradiation single dose; and 4: Ryanodex post-irradiation multiple dose (days 1-5). Groups 1: Control; 2: Ryanodex pre-irradiation; 3: Ryanodex post-irradiation single dose; and 4: Ryanodex post-irradiation multiple dose (days 1-5).
Figure 3:
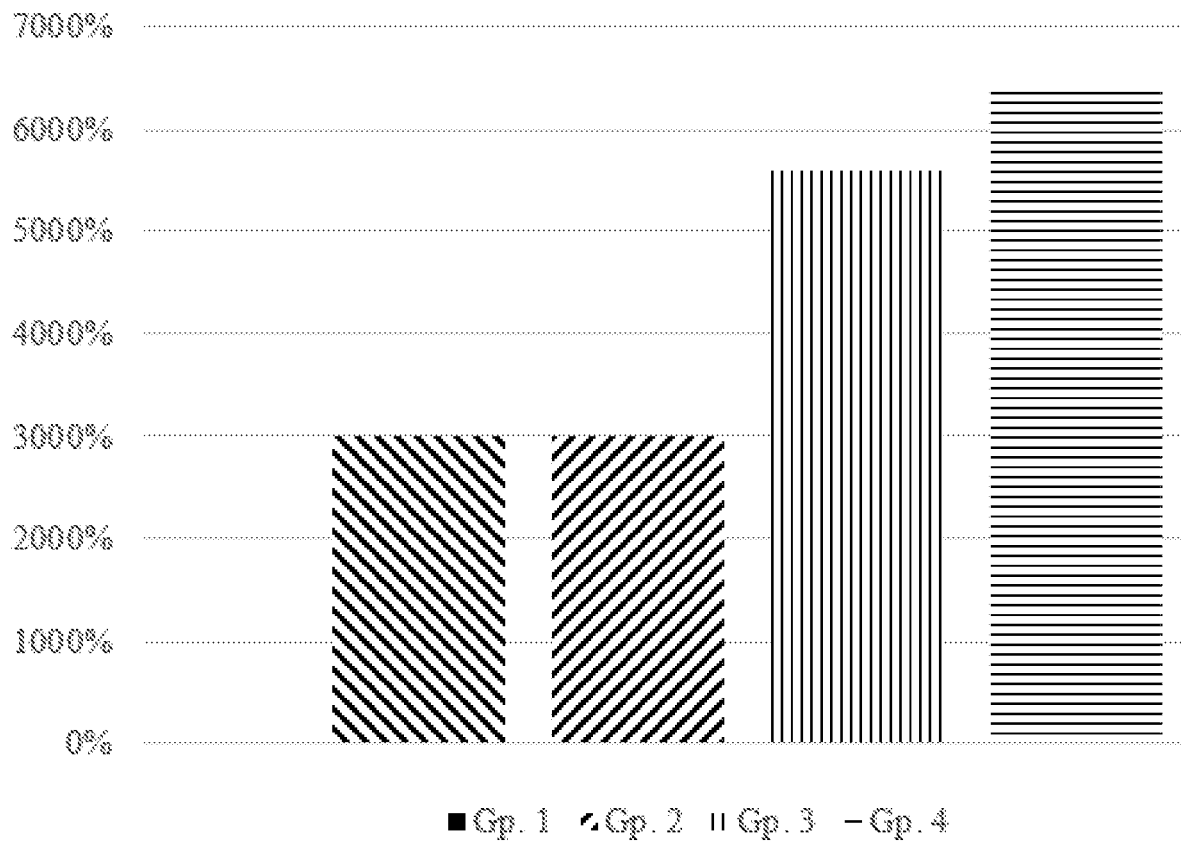
FIG. 3 is a histogram depicting the percent change in blood neutrophils between day 7 and day 30 in Ryanodex-treated animals, groups 1-4. Groups 1: Control; 2: Ryanodex pre-irradiation; 3: Ryanodex post-irradiation single dose; and 4: Ryanodex post-irradiation multiple dose (days 1-5).
Figure 4:
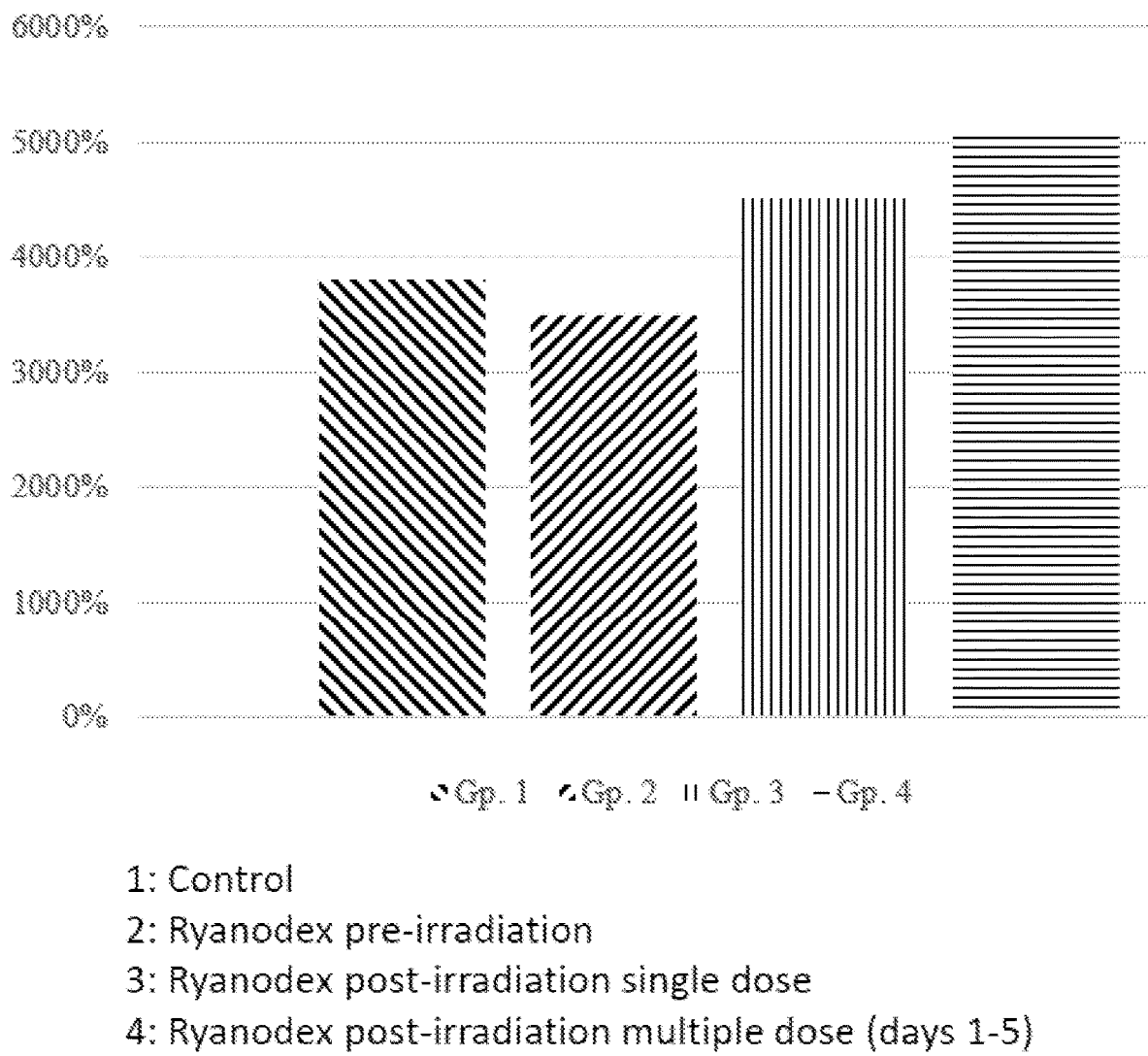
FIG. 4 is a histogram depicting the percent change in blood lymphocytes between day 7 and day 30 in Ryanodex-treated animals, groups 1-4. Groups 1: Control; 2: Ryanodex pre-irradiation; 3: Ryanodex post-irradiation single dose; and 4: Ryanodex post-irradiation multiple dose (days 1-5).
Figure 5:
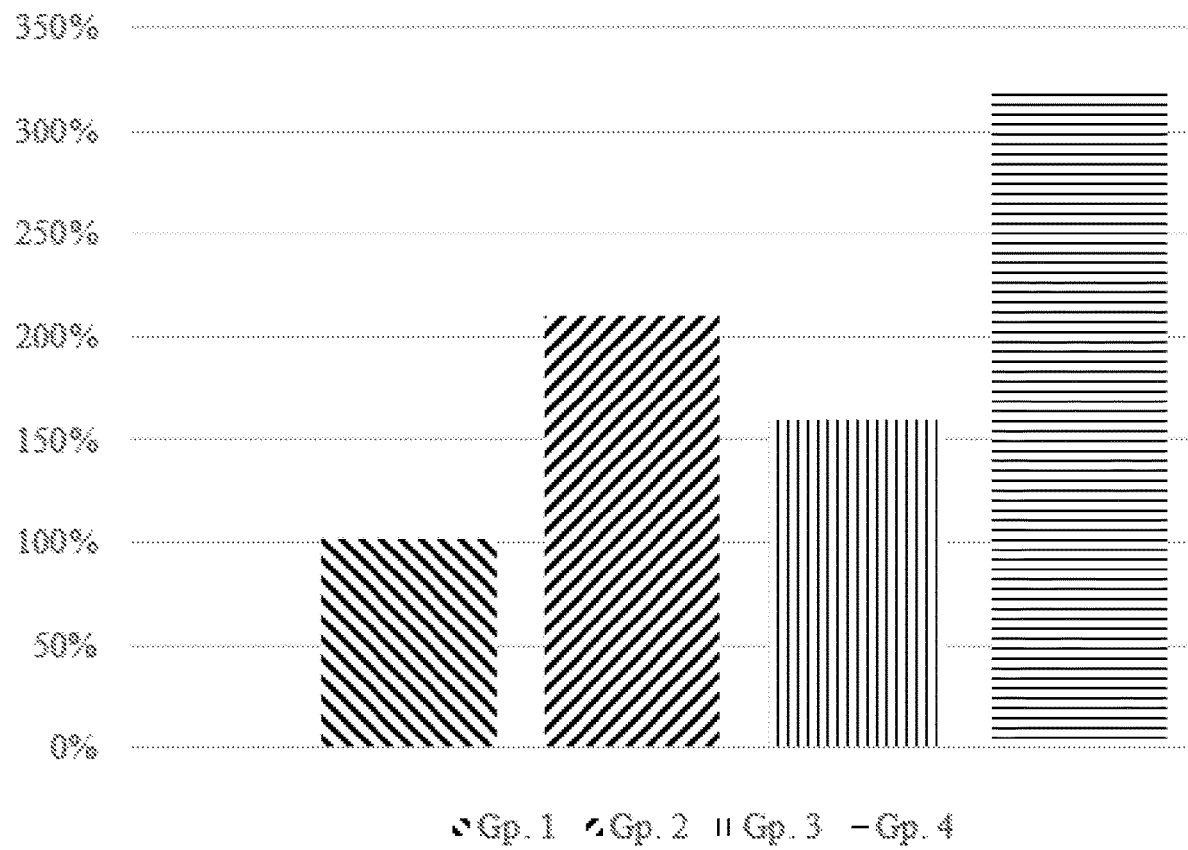
FIG. 5 is a histogram depicting the percent change in blood platelets between day 7 and day 30 in Ryanodex-treated animals, groups 1-4. Groups 1: Control; 2: Ryanodex pre-irradiation; 3: Ryanodex post-irradiation single dose; and 4: Ryanodex post-irradiation multiple dose (days 1-5).

The present disclosure may be understood more readily by reference to the following detailed description taken in connection with the accompanying figures and examples, which form a part of this disclosure. It is to be understood that this disclosure is not limited to the specific compositions or methods described and/or shown herein, and that the terminology used herein is for the purpose of describing particular embodiments by way of example only and is not intended to be limiting of the claimed disclosure. Also, as used in the specification, including the appended claims, the singular forms "a," "an," and "the" include the plural, and reference to a particular numerical value includes at least that particular value, unless the context clearly dictates otherwise. All ranges are inclusive and combinable.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9 to 1.1.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination. Further, reference to values stated in ranges includes each and every value within that range.

As used herein, the term "pharmaceutical composition" shall mean a composition that is suitable for administration to humans and contains pharmaceutically acceptable excipients, e.g., without limitation, stabilizers, bulking agents, buffers, carriers, diluents, vehicles, solubilizers, and binders. As used herein pharmaceutical composition includes, but is not limited to, a liquid form ready for subcutaneous injection or infusion and intramuscular injection.

"Therapeutically effective amount" refers to an amount of an active pharmaceutical agent described herein which is sufficient to inhibit, halt, or cause an improvement in a disorder or condition being treated in a particular subject or subject population. In certain embodiments, in a human or other mammal, a therapeutically effective amount can be determined experimentally in a laboratory or clinical setting, or may be the amount required by government guidelines for the particular disease and subject being treated.

As used herein, "ameliorate" refers to the lessening of the severity in a disorder or condition being treated in a particular subject or subject population.

As used herein, "patient" or "subject" is intended to mean a mammal. Thus, the methods described herein are applicable to human and nonhuman subjects. The methods described herein are particularly applicable to humans.

The term "pharmaceutically acceptable" as used herein means that the thing that is pharmaceutically acceptable, e.g., components, including containers, of a pharmaceutical composition, does not cause unacceptable loss of pharmacological activity or unacceptable adverse side effects. Examples of pharmaceutically acceptable components are provided in The United States Pharmacopeia (USP), The National Formulary (NF), adopted at the United States Pharmacopeial Convention, held in Rockville, Md. in 1990 and FDA Inactive Ingredient Guide 1990, 1996 issued by the U.S. Food and Drug Administration (both are hereby incorporated by reference herein, including any drawings). Other grades of solutions or components that meet necessary limits and/or specifications that are outside of the USP/NF may also be used.

The term "pharmaceutically acceptable salt" as used herein means a salt of a compound of the disclosure that is pharmaceutically acceptable and that possesses the desired pharmacological activity of the parent compound. In particular, such salts are non-toxic, and may be inorganic or organic acid addition salts and base addition salts. Specifically, such salts include: salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

As used herein, the phrases, "resulting from radiation exposure" and "due to radiation exposure" refer to effects that are a direct consequence of radiation exposure, as well as to effects that are a secondary consequence of radiation exposure, as well as to effects that are an indirect consequence of radiation exposure.

The term "$C_1$-$C_6$alk" refers to an aliphatic linker having 1, 2, 3, 4, 5, or 6 carbon atoms and includes, for example, —CH$_2$—, —CH(CH$_3$)—, —CH(CH$_3$)—CH$_2$—, and —C(CH$_3$)$_2$—. The term "—C$_0$alk-" refers to a bond.

The term "alkyl" refers to a straight- or branched-chain hydrocarbon group having from 1 to 12 carbon atoms ("C$_1$-C$_{12}$"), preferably 1 to 6 carbons atoms ("C$_1$-C$_6$"), in the group. Examples of alkyl groups include methyl (Me, C$_1$alkyl), ethyl (Et, C$_2$alkyl), n-propyl (C$_3$alkyl), isopropyl (C$_3$alkyl), butyl (C$_4$alkyl), isobutyl (C$_4$alkyl), sec-butyl (C$_4$alkyl), tert-butyl (C$_4$alkyl), pentyl (C$_5$alkyl), isopentyl (C$_5$alkyl), tert-pentyl (C$_5$alkyl), hexyl (C$_6$alkyl), isohexyl (C$_6$alkyl), and the like.

The term "heterocycloalkyl" refers to any three to ten membered monocyclic or bicyclic, saturated ring structure containing at least one heteroatom selected from the group consisting of O, N and S. Examples of suitable heterocycloalkyl groups include, but are not limited to, azepanyl, aziridinyl, azetidinyl, pyrrolidinyl, piperazinyl, piperidinyl, morpholinyl, thiomorpholinyl, and the like.

The term "aryl" when used alone or as part of a substituent group refers to a mono- or bicyclic-aromatic hydrocarbon ring structure having 6 or 10 carbon atoms in the ring. Preferred aryl moieties include phenyl and naphthyl.

The term "arylene" refers to a mono- or bicyclic-aromatic hydrocarbon ring structure having 6 or 10 carbon atoms in the ring. Preferred arylene moieties include phenylene and naphthylene. Compounds of the disclosure may be chiral and as a result, can exist as a single enantiomer or mixture of enantiomers. All enantiomers and mixtures thereof are contemplated by this disclosure.

Among other things, the disclosure is directed to methods of treating a subject that has been exposed to radiation by administering a pharmaceutical composition comprising dantrolene, or a pharmaceutically acceptable salt thereof. In other aspects, the disclosure is directed to methods of treating a subject that will be exposed to radiation by administering a pharmaceutical composition comprising dantrolene, or a pharmaceutically acceptable salt thereof.

Among other things, the disclosure is directed to methods of treating a subject that has been exposed to radiation by administering a pharmaceutical composition comprising a compound of formula I:

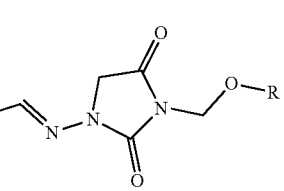

I wherein
R is —P(O)(OH)$_2$ or —P(O)(OR$_1$)(OR$_2$);
R$_1$ is H, —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl; and
R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl,
or a pharmaceutically acceptable salt thereof.

The disclosure is also directed to methods of treating a subject that has been exposed to radiation by administering a pharmaceutical composition comprising a compound of formula II

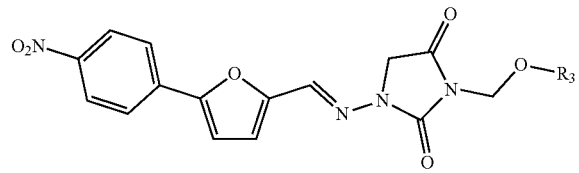

II wherein
R$_3$ is H, —C(O)—Z—N(R$_4$)(R$_5$), —C(O)Z—C(O)—OH, or —C(O)—NH—Y—CH$_2$—OC(O)—Z—C(O)—OH;
Z is C$_{1-6}$alk;
Y is arylene; C$_{1-6}$alkyl;
R$_5$ is H or C$_{1-6}$alkyl; or R$_4$ and R$_5$, together with the nitrogen to which they are attached, form a heterocycloalkyl;
or a pharmaceutically acceptable salt thereof.

Compounds of formula I and II are dantrolene prodrugs and are described in International Patent Application No. PCT/US2018/056713, filed Oct. 19, 2018, the entirety of which is incorporated by reference herein.

In other aspects, the disclosure is directed to methods of treating a subject that will be exposed to radiation by administering a pharmaceutical composition comprising dantrolene, or a pharmaceutically acceptable salt thereof. In other aspects, the disclosure is directed to methods of treating a subject that will be exposed to radiation by administering a pharmaceutical composition comprising a compound of formula I, or a pharmaceutically acceptable salt thereof. In other aspects, the disclosure is directed to methods of treating a subject that will be exposed to radiation by administering a pharmaceutical composition comprising a compound of formula II, or a pharmaceutically acceptable salt thereof.

In other aspects, the disclosure is directed to methods of treating a subject that will be exposed to radiation by administering a pharmaceutical composition comprising dantrolene, a compound of formula I, a compound of formula II, or a pharmaceutically acceptable salt thereof, or a combination thereof.

In some aspects, the dantrolene prodrugs of the disclosure are those wherein R is —P(O)(OH)$_2$ and are of formula I-A:

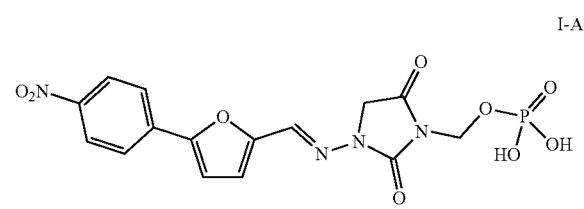 [SMILES: O=C1CN(/N=C/c2ccc(-c3ccc([N+](=O)[O-])cc3)o2)C(=O)N1COP(=O)(O)O]

I-A

Pharmaceutically acceptable salts of compounds of formula I-A are also within the scope of the disclosure. Preferred salts include, for example, sodium salts of compounds of formula I-A. Lithium, magnesium, calcium, and potassium salts of the compounds of formula I-A are also within the scope of the disclosure. Alternative salt forms include ammonium, choline, and tromethamine salts. A preferred salt of the compound of formula I-A is the monosodium salt. Another preferred salt of the compound of formula I-A is the disodium salt. Another preferred salt of the compound of formula I-A is the monotromethamine salt. Another preferred salt of the compound of formula I-A is the tromethanine salt. Also within the scope of the disclosure are pharmaceutically acceptable organic salts of compounds of formula I-A.

In some aspects, the dantrolene prodrugs used in the methods of the disclosure are those wherein R is —P(O)(OR$_1$)(OR$_2$) and are of formula I-B:

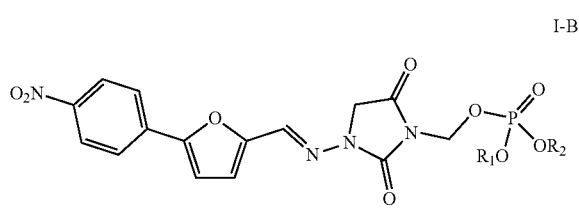

I-B

In some aspects, R$_1$ is H. In these aspects, R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl. Pharmaceutically acceptable salts of such compounds of formula I-B are also within the scope of the disclosure. Preferred salts include, for example, sodium salts of compounds of formula I-B. Other salts include the lithium, magnesium, calcium, and potassium salts of the compounds of formula I-B. Alternative salt forms include ammonium, choline, and tromethamine salts. Also within the scope of the disclosure are pharmaceutically acceptable organic salts of compounds of formula I-B.

In some aspects of compounds of formula I-B, R$_1$ is H and R$_2$ is —C$_{1-26}$alkyl. For example, in some aspects, R$_1$ is H and R$_2$ is —C$_{1-6}$alkyl. In other aspects, R$_1$ is H and R$_2$ is —C$_{1-12}$alkyl. In other aspects, R$_1$ is H and R$_2$ is —C$_{13-26}$alkyl. In other aspects, R$_1$ is H and R$_2$ is —C$_{18-26}$alkyl. In other aspects, R$_1$ is H and R$_2$ is —C$_{20-26}$alkyl. In some aspects, R$_1$ is H and R$_2$ is —C$_1$alkyl. In some aspects, R$_1$ is H and R$_2$ is —C$_2$alkyl. In some aspects, R$_1$ is H and R$_2$ is —C$_3$alkyl. In some aspects, R$_1$ is H and R$_2$ is —C$_4$alkyl. In some aspects, R$_1$ is H and R$_2$ is —C$_5$alkyl. In some aspects, R$_1$ is H and R$_2$ is —C$_6$alkyl. In some aspects, R$_1$ is H and R$_2$ is —C$_7$alkyl. In some aspects, R$_1$ is H and R$_2$ is —C$_8$alkyl. In some aspects, R$_1$ is H and R$_2$ is —C$_9$alkyl. In some aspects, R$_1$ is H and R$_2$ is —C$_{10}$alkyl. In some aspects, R$_1$ is H and R$_2$ is —C$_{11}$alkyl. In some aspects, R$_1$ is H and R$_2$ is —C$_{12}$alkyl. In some aspects, R$_1$ is H and R$_2$ is —C$_{13}$alkyl. In some aspects, R$_1$ is H and R$_2$ is —C$_{14}$alkyl. In some aspects, R$_1$ is H and R$_2$ is —C$_{15}$alkyl. In some aspects, R$_1$ is H and R$_2$ is —C$_{16}$alkyl. In some aspects, R$_1$ is H and R$_2$ is —C$_{17}$alkyl. In some aspects, R$_1$ is H and R$_2$ is —C$_{18}$alkyl. In some aspects, R$_1$ is H and R$_2$ is —C$_{19}$alkyl. In some aspects, R$_1$ is H and R$_2$ is —C$_{20}$alkyl. In some aspects, R$_1$ is H and R$_2$ is —C$_{21}$alkyl. In some aspects, R$_1$ is H and R$_2$ is —C$_{22}$alkyl. In some aspects, R$_1$ is H and R$_2$ is —C$_{23}$alkyl. In some aspects, R$_1$ is H and R$_2$ is —C$_{24}$alkyl. In some aspects, R$_1$ is H and R$_2$ is —C$_{25}$alkyl. In some aspects, R$_1$ is H and R$_2$ is C$_{26}$alkyl.

In some aspects of compounds of formula I-B, R$_1$ is H and R$_2$ is aryl. For example, in some aspects of compounds of formula I-B, R$_1$ is H and R$_2$ is phenyl.

In some aspects of compounds of formula I-B, R$_1$ is H and R$_2$ is C$_{1-6}$alkC(O)O—C$_{1-26}$alkyl. For example, in some aspects, R$_1$ is H and R$_2$ is C$_1$alkC(O)O—C$_{1-26}$alkyl. In other aspects, R$_1$ is H and R$_2$ is C$_2$alkC(O)O—C$_{1-26}$alkyl. In other aspects, R$_1$ is H and R$_2$ is C$_3$alkC(O)O—C$_{1-26}$alkyl. In other aspects, R$_1$ is H and R$_2$ is C$_4$alkC(O)O—C$_{1-26}$alkyl. In other aspects, R$_1$ is H and R$_2$ is C$_5$alkC(O)O—C$_{1-26}$alkyl. In other aspects, R$_1$ is H and R$_2$ is C$_6$alkC(O)O—C$_{1-26}$alkyl. In other aspects, R$_1$ is H and R$_2$ is C$_{1-6}$alkC(O)O—C$_{1-6}$alkyl. In other aspects, R$_1$ is H and R$_2$ is C$_{1-6}$alkC(O)O—C$_{1-12}$alkyl. In other aspects, R$_1$ is H and R$_2$ is C$_{1-6}$alkC(O)O—C$_{13-26}$alkyl. In other aspects, R$_1$ is H and R$_2$ is C$_{1-6}$alkC(O)O—C$_{18-26}$alkyl. In other aspects, R$_1$ is H and R$_2$ is C$_{1-6}$alkC(O)O—C$_{20-26}$alkyl.

In some aspects of compounds of formula I-B, R$_1$ is H and R$_2$ is —C$_1$alkOC(O)C$_{1-26}$alkyl. For example, in some aspects, R$_1$ is H and R$_2$ is —C$_1$alkOC(O)C$_{1-6}$alkyl. In other aspects, R$_1$ is H and R$_2$ is —C$_1$alkOC(O)C$_{1-12}$alkyl. R$_1$ is H and R$_2$ is —C$_1$alkOC(O)C$_{13-16}$alkyl. R$_1$ is H and R$_2$ is —C$_1$alkOC(O)C$_{18-26}$alkyl. R$_1$ is H and R$_2$ is —C$_1$alkOC(O)C$_{20-26}$alkyl.

In some aspects of compounds of formula I-B, R$_1$ is H and R$_2$ is —C$_1$alkOC(O)OC$_{1-26}$alkyl. For example, in some aspects, R$_1$ is H and R$_2$ is —C$_1$alkOC(O)OC$_{1-6}$alkyl. In other aspects, R$_1$ is H and R$_2$ is —C$_1$alkOC(O)OC$_{1-12}$alkyl. In some aspects, R$_1$ is H and R$_2$ is —C$_1$alkOC(O)OC$_{13-16}$alkyl. In some aspects, R$_1$ is H and R$_2$ is —C$_1$alkOC(O)OC$_{18-26}$alkyl. In some aspects, R$_1$ is H and R$_2$ is —C$_1$alkOC(O)OC$_{20-26}$alkyl.

In other aspects of compounds of formula I-B, R$_1$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl and R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl.

In some aspects of compounds of formula I-B, R$_1$ is —C$_{1-26}$alkyl and R$_2$ is —C$_{1-26}$alkyl, aryl, C$_{1-6}$alkC(O)O—C$_{1-26}$alkyl, —C$_1$alkOC(O)C$_{1-26}$alkyl, or C$_1$alkOC(O)OC$_{1-26}$alkyl. For example, in these aspects, R$_1$ can be —C$_{1-6}$alkyl. In other aspects, R$_1$ is —C$_{1-12}$alkyl. In other aspects, R$_1$ is —C$_{13-26}$alkyl. In other aspects, R$_1$ is —C$_{18-26}$alkyl. In other aspects, R$_1$ is —C$_{20-26}$alkyl. In some aspects, R$_1$ is —C$_1$alkyl. In some aspects, R$_1$ is —C$_2$alkyl. In some aspects, R$_1$ is —C$_3$alkyl. In some aspects, R$_1$ is —C$_4$alkyl. In some aspects, R$_1$ is —C$_5$alkyl. In some aspects, R$_1$ is —C$_6$alkyl. In some aspects, R$_1$ is —C$_7$alkyl. In some aspects, R$_1$ is —C$_8$alkyl. In some aspects, R$_1$ is —C$_9$alkyl. In some aspects, R$_1$ is —C$_{10}$alkyl. In some aspects, R$_1$ is —C$_{11}$alkyl. In some aspects, R$_1$ is —C$_{11}$alkyl. In some aspects, R$_1$ is —C$_{13}$alkyl. In some aspects, R$_1$ is —C$_{11}$alkyl. In some aspects, R$_1$ is —C$_{15}$alkyl. In some aspects, R$_1$ is —C$_{16}$alkyl. In some aspects, R$_1$ is —C$_{17}$alkyl. In some aspects, R$_1$ —C$_{18}$alkyl. In some aspects, R$_1$ is —C$_{19}$alkyl. In some aspects, R$_1$ is —C$_{20}$alkyl. In some aspects, $R_1$ is $—C_{21}$alkyl. In some aspects, $R_1$ is $—C_{22}$alkyl. In some aspects, $R_1$ is $—C_{23}$alkyl. In some aspects, $R_1$ is $—C_{24}$alkyl. In some aspects, $R_1$ is $—C_{25}$alkyl. In some aspects, $R_1$ is $—C_{26}$alkyl.

In some aspects of compounds of formula I-B, $R_1$ is aryl and $R_2$ is $—C_{1-26}$alkyl, aryl, $C_{1-6}$alkC(O)O—$C_{1-26}$alkyl, $—C_1$alkOC(O)$C_{1-26}$alkyl, or $C_1$alkOC(O)OC$_{1-26}$alkyl. For example, in some aspects, $R_1$ is phenyl and $R_2$ is $—C_{1-26}$alkyl, aryl, $C_{1-6}$alkC(O)O—$C_{1-26}$alkyl, $—C_1$alkOC(O)$C_{1-26}$alkyl, or $C_1$alkOC(O)OC$_{1-26}$alkyl.

In some aspects of compounds of formula I-B, $R_1$ is $C_{1-6}$alkC(O)O—$C_{1-26}$alkyl and $R_2$ is $—C_{1-26}$alkyl, aryl, $C_{1-6}$alkC(O)O—$C_{1-26}$alkyl, $—C_1$alkOC(O)$C_{1-26}$alkyl, or $C_1$alkOC(O)OC$_1$-26alkyl. For example, in some aspects, $R_1$ is $C_1$alkC(O)O—$C_{1-26}$alkyl. In other aspects, $R_1$ is $C_2$alkC(O)O—$C_{1-26}$alkyl. In other aspects, $R_1$ is $C_3$alkC(O)O—$C_{1-26}$alkyl. In other aspects, $R_1$ is $C_4$alkC(O)O—$C_{1-26}$alkyl. In other aspects, $R_1$ is $C_5$alkC(O)O—$C_{1-26}$alkyl. In other aspects, $R_1$ is $C_6$alkC(O)O—$C_{1-26}$alkyl. In other aspects, $R_1$ is $C_{1-6}$alkC(O)O—$C_{1-6}$alkyl. In other aspects, $R_1$ is $C_{1-6}$alkC(O)O—$C_{1-12}$alkyl. In other aspects, $R_1$ is $C_{1-6}$alkC(O)O—$C_{13-26}$alkyl. In other aspects, $R_1$ is $C_{1-6}$alkC(O)O—$C_{18}$-26alkyl. In other aspects, $R_1$ is $C_{1-6}$alkC(O)O—$C_{20-26}$alkyl.

In some aspects of compounds of formula I-B, $R_1$ is $—C_1$alkOC(O)$C_{1-26}$alkyl and $R_2$ is $—C_{1-26}$alkyl, aryl, $C_{1-6}$alkC(O)O—$C_{1-26}$alkyl, $—C_1$alkOC(O)$C_{1-26}$alkyl, or $C_1$alkOC(O)OC$_{1-26}$alkyl. For example, in some aspects, $R_1$ is $C_1$alkOC(O)$C_{1-6}$alkyl. In other aspects, $R_1$ is $—C_1$alkOC(O)$C_{1-12}$alkyl. In other aspects, $R_1$ is $—C_1$alkOC(O)$C_{13-16}$alkyl. In other aspects, $R_1$ is $—C_1$alkOC(O)$C_{18-26}$alkyl. In other aspects, $R_1$ is $—C_1$alkOC(O)$C_{20-26}$alkyl.

In some aspects of compounds of formula I-B, $R_1$ is $—C_1$alkOC(O)OC$_{1-26}$alkyl and $R_2$ is $—C_{1-26}$alkyl, aryl, $C_{1-6}$alkC(O)O—$C_{1-26}$alkyl, $—C_1$alkOC(O)$C_{1-26}$alkyl, or $C_1$alkOC(O)OC$_{1-26}$alkyl. For example, in some aspects, $R_1$ is $C_1$alkOC(O)OC$_1$-6alkyl. In other aspects, $R_1$ is $—C_1$alkOC(O)OC$_{1-12}$alkyl. In other aspects, $R_1$ is $—C_1$alkOC(O)OC$_{13-16}$alkyl. In other aspects, $R_1$ is $—C_1$alkOC(O)OC$_{18-26}$alkyl. In other aspects, $R_1$ is $—C_1$alkOC(O)OC$_{20-26}$alkyl.

In some aspects, $R_1$ is $—C_{1-26}$alkyl and $R_2$ is $—C_{1-26}$alkyl. For example, in some aspects $R_1$ and $R_2$ are each independently $—C_{1-6}$alkyl, $—C_{1-12}$alkyl, $—C_{13-26}$alkyl, $—C_{18-26}$alkyl, $—C_{20-26}$alkyl, $—C_1$alkyl, $—C_2$alkyl, $—C_3$alkyl, $—C_4$alkyl, $—C_5$alkyl, $—C_6$alkyl, $—C_1$alkyl-$C_5$alkyl, $—C_9$alkyl, $—C_{10}$alkyl, $—C_{11}$alkyl, $—C_{12}$alkyl, $—C_{13}$alkyl, $—C_{14}$alkyl, $—C_{15}$alkyl, $—C_{16}$alkyl, $—C_{17}$alkyl, $—C_{18}$alkyl, $—C_{19}$alkyl, $—C_{20}$alkyl, $—C_{21}$alkyl, $—C_{22}$alkyl, $—C_{23}$alkyl, $—C_{24}$alkyl, $—C_{25}$alkyl, or $—C_{26}$alkyl.

In some aspects, $R_1$ is aryl (e.g., phenyl) and $R_2$ is aryl (e.g., phenyl).

In some aspects, $R_1$ is $C_{1-6}$alkC(O)O—$C_{1-26}$alkyl and $R_2$ is $C_{1-6}$alkC(O)O—$C_{1-26}$alkyl. For example, in some aspects, $R_1$ and $R_2$ are each independently $C_1$alkC(O)O—$C_{1-26}$alkyl, $C_2$alkC(O)O—$C_{1-26}$alkyl, $C_3$alkC(O)O—$C_{1-26}$alkyl, $C_4$alkC(O)O—$C_{1-26}$alkyl, $C_5$alkC(O)O—$C_{1-26}$alkyl, $C_6$alkC(O)O—$C_{1-26}$alkyl, $C_{1-6}$alkC(O)O—$C_{1-6}$alkyl, $C_{1-6}$alkC(O)O—$C_{1-12}$alkyl, $C_{1-6}$alkC(O)O—$C_{13-26}$alkyl, $C_{1-6}$alkC(O)O—$C_{18-26}$alkyl, or $C_{1-6}$alkC(O)O—$C_{20-26}$alkyl.

In some aspects, $R_1$ is $—C_1$alkOC(O)$C_{1-26}$alkyl and $R_2$ is $—C_1$alkOC(O)$C_{1-26}$alkyl. For example, in some aspects, $R_1$ and $R_2$ are each independently $C_1$alkOC(O)$C_{1-6}$alkyl, $—C_1$alkOC(O)$C_{1-12}$alkyl, $—C_1$alkOC(O)$C_{13-16}$alkyl, $—C_1$alkOC(O)$C_{18-26}$alkyl, or $—C_1$alkOC(O)$C_{20-26}$alkyl.

In some aspects, $R_1$ is $—C_1$alkOC(O)OC$_{1-26}$alkyl and $R_2$ is $—C_1$alkOC(O)OC$_{1-26}$alkyl. For example, in some aspects, $R_1$ and $R_2$ are each independently $C_1$alkOC(O)OC$_{1-6}$alkyl, $—C_1$alkOC(O)OC$_{1-12}$alkyl, $—C_1$alkOC(O)OC$_{13-16}$alkyl, $—C_1$alkOC(O)OC$_{18-26}$alkyl, or $—C_1$alkOC(O)OC$_{20-26}$alkyl.

Compounds of formula I, which includes compounds of formula I-A and I-B, can be present as pharmaceutically acceptable salts, where applicable. These salts include sodium salts. Potassium, lithium, calcium, and magnesium salts are also envisioned. Alternative salt forms include ammonium, choline, and tromethamine salts.

Also within the scope of the disclosure are methods of using dantrolene prodrugs of formula II

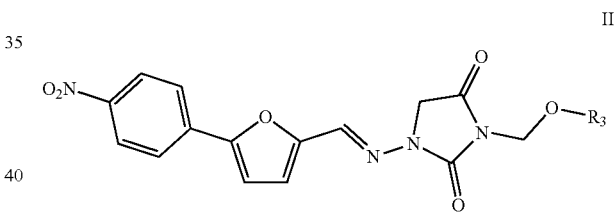

wherein
$R_3$ is H, —C(O)—Z—N($R_4$)($R_5$), —C(O)Z—C(O)—OH, or —C(O)—Y—CH$_2$—OC(O)—Z—C(O)—OH;
Z is $C_{1-6}$alk;
Y is aryl;
$R_4$ is H or $C_{1-6}$alkyl;
$R_5$ is H or $C_{1-6}$alkyl;
or $R_4$ and $R_5$, together with the nitrogen to which they are attached, form a heterocycloalkyl;
or a pharmaceutically acceptable salt thereof.

In preferred aspects, $R_3$ is H and the compound of formula II is a compound of formula II-A

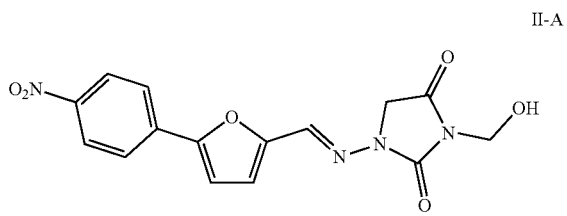 [SMILES: O=C1CN(/N=C/c2ccc(-c3ccc([N+](=O)[O-])cc3)o2)C(=O)N1CO]

or a pharmaceutically acceptable salt thereof.

In other aspects of formula II, $R_3$ is C(O)—Z—N($R_4$)($R_5$) and the compound of formula II is a compound of formula II-B

II-B wherein

Z is $C_{1-6}$alk;

$R_4$ is H or $C_{1-6}$alkyl;

$R_5$ is H or $C_{1-6}$alkyl;

or $R_4$ and $R_5$, together with the nitrogen to which they are attached, form a heterocycloalkyl;

or a pharmaceutically acceptable salt thereof.

In these aspects of formula II-B, Z can be $C_1$alk, $C_2$alk, $C_3$alk, $C_4$alk, $C_5$alk, or $C_6$alk. In some aspects, Z is $C_{1-2}$alk. In some aspects, Z is $C_1$alk.

In these aspects of formula II-B, $R_4$ is H. In other aspects, $R_4$ is $C_{1-6}$alkyl, for example, $C_1$alkyl, $C_2$alkyl, $C_3$alkyl, $C_4$alkyl, $C_5$alkyl, or $C_6$alkyl. In preferred aspects, $R_4$ is methyl, ethyl, or isopropyl.

In these aspects of formula II-B, $R_5$ is H. In other aspects, $R_5$ is $C_{1-6}$alkyl, for example, $C_1$alkyl, $C_2$alkyl, $C_3$alkyl, $C_4$alkyl, $C_5$alkyl, or $C_6$alkyl. In preferred aspects, $R_5$ is methyl, ethyl, or isopropyl.

In some of these aspects of formula II-B, $R_4$ is H and $R_5$ is H. In other aspects, $R_4$ is H and $R_5$ is $C_{1-6}$alkyl, for example, $C_1$alkyl, $C_2$alkyl, $C_3$alkyl, $C_4$alkyl, $C_5$alkyl, or $C_6$alkyl. In yet other aspects, $R_4$ and $R_5$ are each independently $C_{1-6}$alkyl, for example, $C_1$alkyl, $C_2$alkyl, $C_3$alkyl, $C_4$alkyl, $C_5$alkyl, or $C_6$alkyl.

In some of these aspects of formula II-B, $R_4$ and $R_5$, together with the nitrogen to which they are attached, form a heterocycloalkyl. Preferred heterocycloalkyl moieties include, for example, morpholinyl, piperazinyl, piperidinyl, pyrrolidinyl, azetidinyl, and aziridinyl.

Preferred compounds for formula II-B include, for example, and pharmaceutically acceptable salts thereof.

In other aspects of formula II, $R_3$ is C(O)—Z—C(O)—OH and the compound of formula II is a compound of formula II-C

II-C wherein

Z is $C_{1-6}$alk;

or a pharmaceutically acceptable salt thereof.

In these aspects of formula II-C, Z can be $C_1$alk, $C_2$alk, $C_3$alk, $C_4$alk, $C_5$alk, or $C_6$alk. In some aspects, Z is $C_{1-2}$alk. In some aspects, Z is $C_1$alk. In some aspects, Z is $C_2$alk.

A preferred compound of formula II-C is and pharmaceutically acceptable salts thereof.

In other aspects of formula II, $R_3$ is —C(O)—NH—Y—$CH_2$—OC(O)—Z—C(O)—OH and the compound of formula II is a compound of formula II-D

II-D wherein

Y is arylene; and

Z is $C_{1-6}$alk;

or a pharmaceutically acceptable salt thereof.

In these aspects of formula II-D, Y can be phenylene or naphthylene, preferably phenylene.

In these aspects of formula II-D, Z can be $C_1$alk, $C_2$alk, $C_3$alk, $C_4$alk, $C_5$alk, or $C_6$alk. In some aspects, Z is $C_{1-2}$alk. In some aspects, Z is $C_1$alk. In some aspects, Z is $C_2$alk.

A preferred compound of formula II-D is

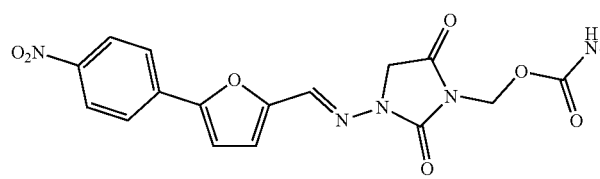

and pharmaceutically acceptable salts thereof.

In other aspects, $R_3$ is —C(O)—O—Y—CH$_2$—OC(O)—Z—C(O)—OH and the compound of formula II is a compound of formula II-E

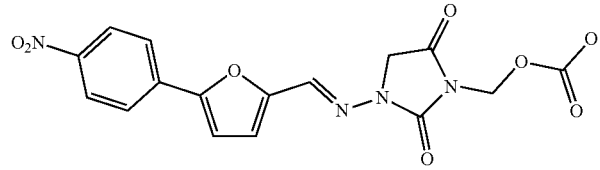

wherein

Y is arylene; and

Z is $C_{1-6}$alk;

or a pharmaceutically acceptable salt thereof.

In these aspects of formula II-E, Y can be phenylene or naphthylene, preferably phenylene.

In these aspects of formula II-E, Z can be $C_1$alk, $C_2$alk, $C_3$alk, $C_4$alk, $C_5$alk, or Chalk. In some aspects, Z is $C_{1-2}$alk. In some aspects, Z is $C_1$alk. In some aspects, Z is $C_2$alk.

Compounds of formula II, which includes compounds of formula II-A, II-B, II-C, II-D, and II-E can be present as pharmaceutically acceptable salts, where applicable. These salts include sodium salts. Potassium, lithium, calcium, and magnesium salts are also envisioned. Alternative salt forms include ammonium, choline, and tromethamine salts. Also within the scope of the disclosure are pharmaceutically acceptable organic salts of compounds of formula II.

Compounds of formula I and II, which includes compounds of formula I-A, I-B, II-A, II-B, II-C, II-D, and II-E and pharmaceutically acceptable salts thereof, can prepared as pharmaceutical compositions by combining the compound with a pharmaceutically acceptable excipient. In some embodiments, the one or more additional pharmaceutically acceptable excipients are selected from the group consisting of preservatives, antioxidants, or mixtures thereof. In yet further embodiments of the disclosure, the additional pharmaceutically acceptable excipient is a preservative such as, but not limited to, phenol, cresol, p-hydroxybenzoic ester, chlorobutanol, or mixtures thereof. In yet further embodiments of the disclosure, the additional pharmaceutically acceptable excipient is an antioxidant such as, but not limited to, ascorbic acid, sodium pyrosulfite, palmitic acid, butylated hydroxyanisole, butylated hydroxytoluene, tocopherols, or mixtures thereof.

Pharmaceutical compositions of the disclosure may be provided as suspensions. In other embodiments, the pharmaceutical compositions of the disclosure may be provided as solutions.

Pharmaceutical compositions used in the methods of the disclosure can have the compound of the disclosure present at a concentration of about 1 mg/ml to about 400 mg/mL, for example, 1 mg/mL to about 200 mg/mL, 1 mg/mL to about 300 mg/mL, preferably 5 mg/mL to about 125 mg/mL, preferably at physiologic pH. In particular embodiments of the disclosure, a compound of the disclosure is present at a concentration equal to or greater than about 5 mg/mL. In further embodiments, a compound of the disclosure is present at a concentration of about 10 to 25 mg/mL. In still further embodiments, a compound of the disclosure is present at a concentration of about 1 mg/mL, 5 mg/mL, 10 mg/mL, 15 mg/mL, 20 mg/mL, 25 mg/mL, 30 mg/mL, 35 mg/mL, 40 mg/mL, 45 mg/mL, or 50 mg/mL. In still further embodiments, a compound of the disclosure is present at a concentration of about 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 375 mg/mL, or about 400 mg/mL.

In certain embodiments, a compound of the disclosure is present at a concentration equal to or greater than about 55 mg/mL. In further embodiments, a compound of the disclosure is present at a concentration of about 55 to 125 mg/mL. In particular embodiments, a compound of the disclosure is present at a concentration of about 75 mg/mL, 80 mg/mL, 85 mg/mL, 90 mg/mL, 95 mg/mL, 100 mg/mL, 105 mg/mL, 110 mg/mL, 115 mg/mL, 120 mg/mL or 125 mg/mL. In other embodiments, a compound of the disclosure is present at a concentration of about 75 mg/mL to 95 mg/mL, 80 mg/mL to 100 mg/mL, 90 mg/mL to 110 mg/ml, 95 mg/mL to 105 mg/mL, 95 mg/mL to 115 mg/mL, 100 mg/mL to 110 mg/mL, 110 mg/mL to 125 mg/mL, including all ranges and subranges there between.

In those aspects directed to methods of treating a subject that "will be" exposed to radiation, the likelihood of the subject being exposed to radiation in the near future (i.e., in about 1 month, in about 2 weeks, in about 7 days, in about 6 days, in about 5, days, in about 4 days, in about 3 days, in about 2 days, in about 1 day), is increased. In some aspects, the likelihood of the subject being exposed to radiation in the near future is certain, that is, the subject's probability of being exposed to radiation in the near future is 100%. In some aspects, the probability of the subject being exposed to radiation in the near future is less than 100%, for example, a 90% probability or greater. In some aspects, the probability of the subject being exposed to radiation in the near future is an 80% probability or greater. In some aspects, the probability of the subject being exposed to radiation in the near future is a 70% probability or greater. In some aspects, the probability of the subject being exposed to radiation in the near future is a 60% probability or greater. In some aspects, the probability of the subject being exposed to radiation in the near future is a 70% probability or greater. In some aspects, the probability of the subject being exposed to radiation in the near future is a 60% probability or greater. In some aspects, the probability of the subject being exposed to radiation in the near future is a 50% probability or greater. In some aspects, the probability of the subject being exposed to radiation in the near future is a 40% probability or greater. In some aspects, the probability of the subject being exposed to radiation in the near future is a 30% probability or greater. In some aspects, the probability of the subject being exposed to radiation in the near future is a 20% probability or greater. In some aspects, the probability of the subject being exposed to radiation in the near future is a 10% probability or greater. In some aspects, the probability of the subject being exposed to radiation in the near future is a 5% probability or greater.

In certain embodiments, pharmaceutical compositions of the disclosure may further comprise a stabilizer or two or more stabilizers. In still further embodiments of the disclosure, the stabilizer is selected from the group consisting of surfactants, polymers, cross-linked polymers, buffering agents, electrolytes, and non-electrolytes. In yet further embodiments of the disclosure, the composition comprises a combination of two or more stabilizers selected from the group consisting of surfactants, polymers, cross-linked polymers, buffering agents, electrolytes, and non-electrolytes. In yet further embodiments of the disclosure, the stabilizer is a surfactant such as, but not limited to, polyethylene oxide (PEO), a PEO derivative, polysorbate 80, polysorbate 20, poloxamer 188, polyethoxylated vegetable oils, lecithin, human serum albumin, and mixtures thereof. In particular embodiments of the disclosure, the stabilizer is a polymer, such as, but not limited to, a polyvinylpyrrolidone (such as, but not limited to povidone K12, povidone K17, and mixtures thereof), polyethylene glycol 3350, and mixtures thereof. In other embodiments of the disclosure, the stabilizer is an electrolyte such as, but not limited to, sodium chloride, calcium chloride, and mixtures thereof. In still other embodiments of the disclosure, the stabilizer is a non-electrolyte, such as, but not limited to, dextrose, glycerol, mannitol, or mixtures thereof. In other embodiments of the disclosure, the stabilizer is a cross-linked polymer such as, but not limited to, carboxymethylcellulose sodium (CMC). In some embodiments of the disclosure, the stabilizer is CMC 7LF, CMC 7MF, CMC 7HF, or mixtures thereof.

In further embodiments of the disclosure, combinations of non-electrolyte stabilizers and electrolyte stabilizers may be used. In some embodiments, the combination of stabilizers may comprise two or more non-electrolyte stabilizers. In other embodiments, the combination of stabilizers may comprise two or more electrolyte stabilizers. In further embodiments, the combination of stabilizers may comprise one or more non-electrolyte stabilizers and one or more electrolyte stabilizers. In yet further embodiments, the combination of stabilizers may comprise two or more of mannitol, dextrose, and sodium chloride.

In certain embodiments of the disclosure, combinations of surfactant stabilizers and polymer stabilizers may be used. In some embodiments, the combination of stabilizers may comprise two or more surfactant stabilizers. In other embodiments, the combination of stabilizers may comprise two or more polymer stabilizers. In further embodiments, the combination of stabilizers may comprise one or more surfactant stabilizers and one or more polymer stabilizers. In yet further embodiments, the combination of stabilizers may comprise two or more of polysorbate 80, polysorbate 20, and poloxamer 188. In still further embodiments, the combination of stabilizers may comprise one or more of polysorbate 80, polysorbate 20, and poloxamer 188 and one or more of povidone K12, povidone K17, and polyethylene glycol 3350.

In certain embodiments of the disclosure, the composition comprises about 0.2 mg/mL to about 75 mg/mL of the one or more stabilizers, and all ranges and subranges therebetween. In particular embodiments of the disclosure, the composition comprises about 0.2 to 0.7 mg/mL, 0.5 to 1 mg/mL, 1 to 5 mg/mL, 2 to 8 mg/mL, 5 to 6 mg/mL, 5 to 10 mg/mL, 8 to 12 mg/mL, 10 to 15 mg/mL, 15 to 20 mg/mL, 20 to 30 mg/mL, 30 to 40 mg/mL, 40 to 50 mg/mL, 45 to 55 mg/mL, 50 to 60 mg/mL, or 60 to 75 mg/mL of one or more stabilizers, and all ranges and subranges there between. In further embodiments of the disclosure, the composition comprises about 0.2 mg/mL, 0.5 mg/mL, 1 mg/mL, 2 mg/mL, 3 mg/mL, 4 mg/mL, 5 mg/mL, 5.5 mg/mL, 6 mg/mL, 7 mg/mL, 8 mg/mL, 9 mg/mL, 10 mg/mL, 12 mg/mL, 15 mg/mL, 17 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, or 75 mg/mL of one or more stabilizers.

In particular embodiments of the disclosure, the composition further comprises one or more buffering agents, such as, but not limited to, $NaH_2PO_4 \cdot H_2O$, $NaH_2PO_4 \cdot 2H_2O$, anhydrous $NaH_2PO_4$, sodium citrate, citric acid, Tris, sodium hydroxide, HCl, or mixtures thereof. In certain embodiments of the disclosure, the composition comprises about 1 mM to 20 mM of one or more buffering agents, and all ranges and subranges therebetween. In particular embodiments of the disclosure, the composition comprises about 1 to 2 mM, 1 to 3 mM, 1 to 5 mM, 2 to 8 mM, 5 to 6 mM, 5 to 10 mM, 8 to 12 mM, 10 to 15 mM, or 15 to 20 mM of one or more buffering agents, and all ranges and subranges therebetween. In further embodiments of the disclosure, the composition comprises about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM of one or more buffering agents.

In certain embodiments of the disclosure, a pharmaceutical composition has a pH of from about 3-10, for example, 3, 4, 5, 6, 7, 8, 9, or 10. In further embodiments of the disclosure, the composition has a pH of from about 5-9. In further embodiments of the disclosure, the composition has a pH of from about 6 to 9. In further embodiments of the disclosure, the composition has a pH of from about 6 to 7. In further embodiments of the disclosure, the composition has a pH of from about 6 to 8.5. In further embodiments of the disclosure, the composition has a pH of from about 7 to 8.5. In further embodiments of the disclosure, the composition has a pH of from over 7 to 8.5. In certain embodiments of the disclosure, the composition has a pH of about 6.0 to 8.0. In particular embodiments of the disclosure, the composition has a pH of about 6.0 to 7.0, 6.5 to 7.0, 6.5 to 7.5, 6.7 to 7.2, 7.0 to 7.2, 7.0 to 7.5, 7.0 to 8.0 or 7.0 to 8.5

In certain embodiments of the disclosure, a pharmaceutical composition has an osmolarity from about 280 mOsm/L to about 310 mOsm/L, for example, about 280, 285, 290, 300, 305, or about 310 mOsm/L. In further embodiments of the disclosure, the composition has an osmolarity from about 290 mOsm/L to about 300 mOsm/L. In yet further embodiments of the disclosure, the composition has an osmolarity of about 290 mOsm/L. In some embodiments, the osmolarity may be selected through the use of appropriate amounts of one or more stabilizers that act as tonicifiers in a composition, such as, but not limited to, the non-electrolyte stabilizers and electrolyte stabilizers described herein. In some embodiments, the osmolarity may be selected through the use of appropriate amounts of one or more buffering agents that act as tonicifiers in a composition, such as, but not limited to, the buffering agents described herein.

In those aspects directed to methods of treating a subject that "will be" exposed to radiation, the likelihood of the subject being exposed to radiation in the near future (i.e., in about 1 month, in about 2 weeks, in about 7 days, in about 6 days, in about 5, days, in about 4 days, in about 3 days, in about 2 days, in about 1 day), is a result of a radiation as a treatment for cancer.

In those aspects directed to methods of treating a subject that "will be" exposed to radiation, the likelihood of the subject being exposed to radiation in the near future (i.e., in about 1 month, in about 2 weeks, in about 7 days, in about 6 days, in about 5, days, in about 4 days, in about 3 days, in about 2 days, in about 1 day), is a result of nuclear power plant leakage exposure. In these aspects, the integrity of the nuclear power plant is such that the likelihood of a leakage in the near future is elevated. In some aspects, the subject is within a 100 mile radius of the nuclear power plant leakage site. In some aspects, the subject is within a 75 mile radius of the nuclear power plant leakage site. In some aspects, the subject is within a 50 mile radius of the nuclear power plant leakage site. In some aspects, the subject is within a 40 mile radius of the nuclear power plant leakage site. In some aspects, the subject is within a 30 mile radius of the nuclear power plant leakage site. In some aspects, the subject is within a 20 mile radius of the nuclear power plant leakage site. In some aspects, the subject is within a 10 mile radius of the nuclear power plant leakage site. In some aspects, the subject is within a 9 mile radius of the nuclear power plant leakage site. In some aspects, the subject is within an 8 mile radius of the nuclear power plant leakage site. In some aspects, the subject is within a 7 mile radius of the nuclear power plant leakage site. In some aspects, the subject is within a 6 mile radius of the nuclear power plant leakage site. In some aspects, the subject is within a 5 mile radius of the nuclear power plant leakage site. In some aspects, the subject is within a 4 mile radius of the nuclear power plant leakage site. In some aspects, the subject is within a 3 mile radius of the nuclear power plant leakage site. In some aspects, the subject is within a 2 mile radius of the nuclear power plant leakage site. In some aspects, the subject is within a 1 mile radius of the nuclear power plant leakage site. In some aspects, the subject is located at the nuclear power plant leakage site.

In those aspects directed to methods of treating a subject that "will be" exposed to radiation, the likelihood of the subject being exposed to radiation in the near future (i.e., in about 1 month, in about 2 weeks, in about 7 days, in about 6 days, in about 5, days, in about 4 days, in about 3 days, in about 2 days, in about 1 day), is a result of a nuclear weapon detonation. In these aspects, the likelihood of a nuclear weapon detonation is elevated. In some aspects, the likelihood of a nuclear weapon detonation can be elevated due to terroristic threats. In some aspects, the likelihood of a nuclear weapon detonation can be elevated due to identification of a nuclear weapon launch. In some aspects, the subject is within a 100 mile radius of a nuclear weapon detonation. In some aspects, the subject is within a 75 mile radius of a nuclear weapon detonation. In some aspects, the subject is within a 50 mile radius of a nuclear weapon detonation. In some aspects, the subject is within a 40 mile radius of a nuclear weapon detonation. In some aspects, the subject is within a 30 mile radius of a nuclear weapon detonation. In some aspects, the subject is within a 20 mile radius of a nuclear weapon detonation. In some aspects, the subject is within a 10 mile radius a nuclear weapon detonation. In some aspects, the subject is within a 9 mile radius of a nuclear weapon detonation. In some aspects, the subject is within an 8 mile radius of a nuclear weapon detonation. In some aspects, the subject is within a 7 mile radius of a nuclear weapon detonation. In some aspects, the subject is within a 6 mile radius of a nuclear weapon detonation. In some aspects, the subject is within a 5 mile radius of a nuclear weapon detonation. In some aspects, the subject is within a 4 mile radius of a nuclear weapon detonation. In some aspects, the subject is within a 3 mile radius of a nuclear weapon detonation. In some aspects, the subject is within a 2 mile radius of a nuclear weapon detonation In some aspects, the subject is within a 1 mile radius of a nuclear weapon detonation.

The methods of the disclosure are preferably used in the treatment of mammals. In more preferred aspects, the methods of the disclosure are used for the treatment of humans.

The radiation exposure that can be treated (either pre-exposure or post-exposure) includes any type of radiation exposure that is above ambient radiation exposure. In some aspects, the radiation exposure is a dose of penetrating radiation. In some aspects, the radiation exposure is a dose of penetrating radiation over a time period that is 60 minutes or less, for example, about 1, 2, 3, 4, 5, 6, 7, 8, 9, 10, 11, 12, 13, 14, 15, 16, 17, 18, 19, 20, 25, 30, 35, 40, 45, 50, 55, or about 60 minutes. In some aspects, the radiation exposure is sufficient to result in depletion of immature parenchymal stem cells in a control subject, not treated according to the disclosed methods. In some aspects, the radiation exposure is a dose of penetrating radiation over a time period that is greater than 60 minutes, for example, 2, 3, 4, 5, 6, 7, 8 hours, or longer.

In some aspects, the subject has been exposed to chemoradiation. In some aspects, the subject has been diagnosed with cancer and has been exposed to radiation in an amount sufficient to treat the subject's cancer. In some aspects, the subject will be exposed to chemoradiation. In some aspects, the subject has been diagnosed with cancer and will be exposed to radiation in an amount sufficient to treat the subject's cancer.

In some aspects, the subject has been exposed to radiation that results from nuclear power plant leakage. In some aspects, the subject will be exposed to radiation that results from nuclear power plant leakage.

In some aspects, the subject has been exposed to radiation that results from nuclear weapon exposure. In some aspects, the subject will be exposed to radiation that results from nuclear weapon exposure.

In some aspects, the radiation is X-ray radiation, gamma ray radiation, neutron radiation, or a combination thereof. In some aspects, the radiation is X-ray radiation. In some aspects, the radiation is gamma ray radiation. In some aspects, the radiation is neutron radiation.

In some aspects, the subject has been exposed to a radiation dose that is above ambient level. In some aspects, the subject has been exposed to a radiation dose of at least 0.3 Gy. In some aspects, the subject has been exposed to a radiation dose of at least 0.7 Gy. In some aspects, the subject has been exposed to a radiation dose of at least 6 Gy. In some aspects, the subject has been exposed to a radiation dose of at least 10 Gy. In some aspects, the subject has been exposed to a radiation dose of at least 50 Gy. In some aspects, the subject has been exposed to a radiation dose that is between 0.3 Gy and 50 Gy. In some aspects, the subject has been exposed to a radiation dose that is between 0.7 Gy and 50 Gy. In some aspects, the subject has been exposed to a radiation dose that is between 0.3 Gy and 0.7 Gy. In some aspects, the subject has been exposed to a radiation dose that is between 0.3 Gy and 6 Gy. In some aspects, the subject has been exposed to a radiation dose that is between 0.3 Gy and 10 Gy. In some aspects, the subject has been exposed to a radiation dose that is between 0.7 Gy and 6 Gy. In some aspects, the subject has been exposed to a radiation dose that is between 0.7 Gy and 10 Gy. In some aspects, the subject has been exposed to a radiation dose that is between 0.7 Gy and 50 Gy. In some aspects, the subject has been exposed to a radiation dose that is 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 Gy.

In some aspects, the subject will be exposed to a radiation dose that is above ambient level. In some aspects, the subject will be exposed to a radiation dose of at least 0.3 Gy. In some aspects, the subject will be exposed to a radiation dose of at least 0.7 Gy. In some aspects, the subject will be exposed to a radiation dose of at least 6 Gy. In some aspects, the subject will be exposed to a radiation dose of at least 10 Gy. In some aspects, the subject will be exposed to a radiation dose of at least 50 Gy. In some aspects, the subject will be exposed to a radiation dose that is between 0.3 Gy and 50 Gy. In some aspects, the subject will be exposed to a radiation dose that is between 0.7 Gy and 50 Gy. In some aspects, the subject will be exposed to a radiation dose that is between 0.3 Gy and 0.7 Gy. In some aspects, the subject will be exposed to a radiation dose that is between 0.3 Gy and 6 Gy. In some aspects, the subject will be exposed to a radiation dose that is between 0.3 Gy and 10 Gy. In some aspects, the subject will be exposed to a radiation dose that is between 0.7 Gy and 6 Gy. In some aspects, the subject will be exposed to a radiation dose that is between 0.7 Gy and 10 Gy. In some aspects, the subject will be exposed to a radiation dose that is between 0.7 Gy and 50 Gy. In some aspects, the subject will be exposed to a radiation dose that is 0.3, 0.4, 0.5, 0.6, 0.7, 0.8, 2.3, 2.4, 2.5, 2.6, 2.7, 2.8, 2.9, 3, 4.5, 4.6, 4.7, 4.8, 4.9, 5, 5.1, 5.2, 6.7, 6.8, 6.9, 7, 7.1, 7.2, 7.3, 7.4, 8.9, 9, 9.1, 9.2, 9.3, 9.4, 9.5, 9.6, 22, 23, 24, 25, 26, 27, 28, 29, 30, 47, 48, 49 or about 50 Gy.

The amount of dantrolene, dantrolene prodrug, or a pharmaceutically acceptable salt thereof, that is therapeutically effective to treat the subject according to any of the described methods should be determined by a practitioner skilled in the art. The therapeutically effective amount can be the amount needed to treat the subject with a single dose. Alternatively, the therapeutically effective amount can be the cumulative amount of dantrolene needed to treat the subject with more than one dose, for example multiple doses, over a chronic or prolonged course of treatment.

In some aspects, the therapeutically effective amount of the dantrolene, dantrolene prodrug, or a pharmaceutically acceptable salt thereof, is 1 mg/kg to about 30 mg/kg, administered in one or two doses. In other aspects, the therapeutically effective amount of dantrolene, dantrolene prodrug, or a pharmaceutically acceptable salt thereof, is 1 mg/kg to about 20 mg/kg. In other aspects, the therapeutically effective amount of dantrolene, dantrolene prodrug, or a pharmaceutically acceptable salt thereof, is about 5 mg/kg to about 30 mg/kg. In other aspects, the therapeutically effective amount of dantrolene, dantrolene prodrug, or a pharmaceutically acceptable salt thereof, is about 10 mg/kg to about 30 mg/kg. In other aspects, the therapeutically effective amount of dantrolene, dantrolene prodrug, or a pharmaceutically acceptable salt thereof, is about 15 mg/kg to about 30 mg/kg. In other aspects, the therapeutically effective amount of dantrolene, dantrolene prodrug, or a pharmaceutically acceptable salt thereof, is about 20 mg/kg to about 30 mg/kg. In other aspects, the therapeutically effective amount of dantrolene, dantrolene prodrug, or a pharmaceutically acceptable salt thereof, is about 5 mg/kg to about 20 mg/kg. In other aspects, the therapeutically effective amount of 0.9, 1, 1.1, 1.2, 1.3, 1.4, 1.5, 1.6, 1.7, 1.8, 1.9, 2, 2.1, 2.2, 3.1, 3.2, 3.3, 3.4, 3.5, 3.6, 3.7, 3.8, 3.9, 4, 4.1, 4.2, 4.3, 4.4, 5.3, 5.4, 5.5, 5.6, 5.7, 5.8, 5.9, 6, 6.1, 6.2, 6.3, 6.4, 6.5, 6.6, 7.5, 7.6, 7.7, 7.8, 7.9, 8, 8.1, 8.2, 8.3, 8.4, 8.5, 8.6, 8.7, 8.8, 9.7, 9.8, 9.9, 10, 11, 12, 13, 14, 15, 16, 17, 18, 19, 20, 21, 31, 32, 33, 34, 35, 36, 37, 38, 39, 40, 41, 42, 43, 44, 45, 46, dantrolene, dantrolene prodrug, or a pharmaceutically acceptable salt thereof, is about 5 mg/kg to about 15 mg/kg. In other aspects, the therapeutically effective amount of dantrolene, dantrolene prodrug, or a pharmaceutically acceptable salt thereof, is about 5 mg/kg to about 10 mg/kg. In other aspects, the therapeutically effective amount of dantrolene, dantrolene prodrug, or a pharmaceutically acceptable salt thereof, is about 10 mg/kg to about 20 mg/kg. In other aspects, the therapeutically effective amount of dantrolene, dantrolene prodrug, or a pharmaceutically acceptable salt thereof, is about 2 mg/kg to about 10 mg/kg, preferably from about 2 mg/kg to about 6 mg/kg. In other aspects, the therapeutically effective amount of dantrolene, dantrolene prodrug, or a pharmaceutically acceptable salt thereof, is about 15 mg/kg to about 20 mg/kg. In other aspects, the therapeutically effective amount of dantrolene, dantrolene prodrug, or a pharmaceutically acceptable salt thereof, is about 1, 2, 3, 4, 5, 6, 7, 8, 9, 10, 11, 12, 13, 14, 15, 16, 17, 18, 19, 20, 21, 22, 23, 24, 25, 26, 27, 28, 29, or about 30 mg/kg. In some embodiments, the therapeutically effective amount of dantrolene, dantrolene prodrug, or a pharmaceutically acceptable salt thereof, is greater than 30 mg/kg, for example, 30 mg/kg to about 100 mg/kg, administered in one or two doses. In some aspects, the therapeutically effective amount of dantrolene, dantrolene prodrug, or a pharmaceutically acceptable salt thereof, is about 35, 40, 45, 50, 55, 60, 65, 70, 75, 80, 85, 90, 95, or about 100 mg/kg.

In some aspects of the disclosure, the timing of the administration of the pharmaceutical composition comprising dantrolene, dantrolene prodrug, or a pharmaceutically acceptable salt thereof, to the subject, after exposure to radiation, can affect treatment.

Compositions comprising dantrolene, dantrolene prodrug, or a pharmaceutically acceptable salt thereof, can be administered chronically to the subject, in two or more doses, that is, over the course of two or more weeks, for example, 2, 3, 4, 5, 6, 7, 8 or more weeks, after the subject has been exposed to the radiation. Compositions comprising dantrolene, dantrolene prodrug, or a pharmaceutically acceptable salt thereof, can be administered acutely to the subject, in one or more doses, that is, over the course of less than two weeks, for example, over the course of hours or days, for example, over 1, 2, 3, 4, 5, 6, 7, 8, 9, 10, 11, 12, 13, 14, 15, 16, 17, 18, 19, 20, 21, 22, 23, or 24 hours or over 2, 3, 4, 5, 6, 7, 8, 9, 10, 11, 12, or 13 days, after the subject has been exposed to the radiation.

Regarding the timing of the pharmaceutical composition comprising dantrolene, dantrolene prodrug, or a pharmaceutically acceptable salt thereof, in some aspects, the pharmaceutical composition comprising dantrolene, dantrolene prodrug, or a pharmaceutically acceptable salt thereof, at least one dose is administered to the subject 24 hours or less after the subject has been exposed to the radiation. In some aspects, the pharmaceutical composition comprising dantrolene, dantrolene prodrug, or a pharmaceutically acceptable salt thereof, at least one dose is administered to the subject 20 hours or less after the subject has been exposed to the radiation. In some aspects, the pharmaceutical composition comprising dantrolene, dantrolene prodrug, or a pharmaceutically acceptable salt thereof, at least one dose is administered to the subject 16 hours or less after the subject has been exposed to the radiation. In some aspects, the pharmaceutical composition comprising dantrolene, dantrolene prodrug, or a pharmaceutically acceptable salt thereof, at least one dose is administered to the subject 12 hours or less after the subject has been exposed to the radiation. In some aspects, the pharmaceutical composition comprising dantrolene, dantrolene prodrug, or a pharmaceutically acceptable salt thereof, at least one dose is administered to the subject 8 hours or less after the subject has been exposed to the radiation. In some aspects, the pharmaceutical composition comprising dantrolene, dantrolene prodrug, or a pharmaceutically acceptable salt thereof, at least one dose is administered to the subject 4 hours or less after the subject has been exposed to the radiation. In some aspects, the pharmaceutical composition comprising dantrolene, dantrolene prodrug, or a pharmaceutically acceptable salt thereof, at least one dose is administered to the subject 2 hours or less after the subject has been exposed to the radiation. In some aspects, the pharmaceutical composition comprising dantrolene, dantrolene prodrug, or a pharmaceutically acceptable salt thereof, at least one dose is administered to the subject 1 hour or less after the subject has been exposed to the radiation. In some aspects, the pharmaceutical composition comprising dantrolene, dantrolene prodrug, or a pharmaceutically acceptable salt thereof, at least one dose is administered to the subject within about 1, 2, 3, 4, 5, 6, 7, 8, 9, 10, 11, 12, 13, 14, 15, 16, 17, 18, 19, 20, 21, 22, 23, or within about 24 hours after the subject has been exposed to radiation.

Regarding the timing of the pharmaceutical composition comprising dantrolene prodrug or a pharmaceutically acceptable salt thereof, in some aspects, the pharmaceutical composition comprising dantrolene prodrug or a pharmaceutically acceptable salt thereof, at least one dose is administered to the subject 24 hours or more before the subject is exposed to the radiation. In some aspects, the pharmaceutical composition comprising dantrolene, dantrolene prodrug, or a pharmaceutically acceptable salt thereof, at least one dose is administered to the subject 20 hours or more before the subject is exposed to the radiation. In some aspects, the pharmaceutical composition comprising dantrolene, dantrolene prodrug, or a pharmaceutically acceptable salt thereof, at least one dose is administered to the subject 16 hours or more before the subject is exposed to the radiation. In some aspects, the pharmaceutical composition comprising dantrolene, dantrolene prodrug, or a pharmaceutically acceptable salt thereof, at least one dose is administered to the subject 12 hours or more before the subject is exposed to the radiation. In some aspects, the pharmaceutical composition comprising dantrolene, dantrolene prodrug, or a pharmaceutically acceptable salt thereof, at least one dose is administered to the subject 8 hours or more before the subject is exposed to the radiation. In some aspects, the pharmaceutical composition comprising dantrolene, dantrolene prodrug, or a pharmaceutically acceptable salt thereof, at least one dose is administered to the subject 4 hours or more before the subject is exposed to the radiation. In some aspects, the pharmaceutical composition comprising dantrolene, dantrolene prodrug, or a pharmaceutically acceptable salt thereof, at least one dose is administered to the subject 2 hours or more before the subject is exposed to the radiation. In some aspects, the pharmaceutical composition comprising dantrolene, dantrolene prodrug, or a pharmaceutically acceptable salt thereof, at least one dose is administered to the subject 1 hour or more before the subject is exposed to the radiation. In some aspects, the pharmaceutical composition comprising dantrolene, dantrolene prodrug, or a pharmaceutically acceptable salt thereof, at least one dose is administered to the subject about 1, 2, 3, 4, 5, 6, 7, 8, 9, 10, 11, 12, 13, 14, 15, 16, 17, 18, 19, 20, 21, 22, 23, or about 24 hours before the subject is exposed to radiation.

While in some aspects, the pharmaceutical composition comprising dantrolene, dantrolene prodrug, or a pharmaceutically acceptable salt thereof, can deliver the therapeutically effective amount of dantrolene (or a dantrolene metabolite such as 5-hydroxy dantrolene) to the radiation-exposed subject in one dose. In other aspects, two or more doses of the pharmaceutical composition may be needed to deliver the therapeutically effective amount of dantrolene to the radiation-exposed subject. For example, 2, 3, 4, 5, 6, 7, 8, 9, or 10 doses of the pharmaceutical composition may be needed to deliver the therapeutically effective amount of dantrolene to the radiation-exposed subject. These additional dosages can be administered substantially concurrently with the first dose. In other aspects, the additional dosages are separated in time from the first dose. In those aspects wherein 3 or more doses are administered, each dose can be separated in time from the administration of any other dose.

In some aspects of the disclosure, the administration of dantrolene to the radiation-exposed subject is an adjunct therapy for radiation exposure. Subjects exposed to radiation can also be administered one or more radiation therapies.

The pharmaceutical composition comprising dantrolene, dantrolene prodrug, or a pharmaceutically acceptable salt thereof can be administered intravenously. In other aspects, the pharmaceutical composition comprising dantrolene, dantrolene prodrug, or a pharmaceutically acceptable salt thereof can be administered transdermally. In other aspects, the pharmaceutical composition comprising dantrolene, dantrolene prodrug, or a pharmaceutically acceptable salt thereof can be administered intramuscularly. In other aspects, the pharmaceutical composition comprising dantrolene, dantrolene prodrug, or a pharmaceutically acceptable salt thereof can be administered intraosseously. In other aspects, the pharmaceutical composition comprising dantrolene, dantrolene prodrug, or a pharmaceutically acceptable salt thereof can be administered subcutaneously.

Preferred pharmaceutical compositions for use in the described methods include dantrolene, dantrolene prodrug, or a pharmaceutically acceptable salt thereof, and one or more pharmaceutically acceptable excipients. Preferred pharmaceutical compositions comprise dantrolene, dantrolene prodrug, or a pharmaceutically acceptable salt thereof, mannitol, a polysorbate (e.g., polysorbate 80), a povidone (e.g. povidone K12), an optional pH adjustor (e.g. NaOH or HCl), and water.

A particularly preferred pharmaceutical composition comprising dantrolene, or a pharmaceutically acceptable salt thereof is RYANODEX® (dantrolene sodium, Eagle Pharmaceuticals, Woodcliff Lake, NJ). RYANODEX® is an injectable suspension provided as a sterile lyophilized powder. It is supplied in 20 mL vials containing 250 mg dantrolene sodium, 125 mg mannitol, 25 mg polysorbate 80, 4 mg povidone K12, and sufficient sodium hydroxide or hydrochloric acid for pH adjustment. When reconstituted with 5 mL sterile water for injection USP, this yields a suspension.

The methods of the disclosure result in a lower mortality of the subject as a result of radiation exposure, as compared to a control subject that is not treated according to any described method.

In some aspects, treatment according to a method of the disclosure improves at least one hematological parameter of the subject, as compared to a control subject that is not treated according to any described method. Hematological parameters include, for example, White Blood Cells, Red Blood Cells, Hemoglobin, Hematocrit, Mean Corpuscular Volume, Mean Corpuscular Hemoglobin, Mean Corpuscular Hemoglobin Concentration, Red Cell Distribution Width, Platelets, Mean Platelet Volume, Differential leukocyte count (absolute), Neutrophils Absolute, Lymphocytes Absolute, Monocytes Absolute, Eosinophils Absolute, Basophils Absolute, Reticulocyte Percent, and Reticulocyte Absolute Count.

In some aspects, treatment according to a method of the disclosure is effective for treating hematopoietic syndrome occurring in the subject as a result of the radiation exposure.

In some aspects, treatment according to a method of the disclosure is effective for treating gastrointestinal syndrome occurring in the subject as a result of the radiation exposure.

In some aspects, treatment according to a method of the disclosure is effective for treating cardiovascular syndrome occurring in the subject as a result of the radiation exposure.

In some aspects, treatment according to a method of the disclosure is effective for treating central nervous system syndrome occurring in the subject as a result of the radiation exposure.

Isotopic variants of the compounds of the disclosure are also within the scope of the disclosure. As used herein, the term "isotopic variant" refers to a compound that contains proportions of isotopes at one or more of the atoms that constitute such compound, in greater than natural abundance. For example, an "isotopic variant" of a compound can be radiolabeled, that is, contain one or more radioactive isotopes, or can be labeled with non radioactive isotopes such as for example, deuterium ($^2$H or D), carbon-11 ($^{11}$C), carbon-13 ($^{13}$C), nitrogen-15 ($^{15}$N), fluoride-18 ($^{18}$F), or the like. It will be understood that, in a compound where such isotopic substitution is made, the following atoms, where present, may vary, so that for example, any hydrogen may be $^2$H/D, any carbon may be $^{11}$C or $^{13}$C, any nitrogen may be $^{15}$N, or any fluoride (if present) may be $^{18}$F, and that the presence and placement of such atoms may be determined within the skill of the art.

EXAMPLES

The following examples are provided to illustrate some of the concepts described within this disclosure. While each example is considered to provide specific individual embodiments of disclosure, none of the Examples should be considered to limit the more general embodiments described herein. In the following examples, efforts have been made to ensure accuracy with respect to numbers used (e.g. amounts, temperature, etc.) but some experimental error and deviation should be accounted for.

Example 1. Radiation Dosing Study

Study Objective. To evaluate the efficacy of intravenous administration of Ryanodex to prevent or mitigate acute radiation syndrome in a total body irradiated C57BL/6 male mouse hematopoietic model.

Radiation and Dosimetry. For total body irradiation dose administration, animals were irradiated in the RS-2000 X-ray Biological Irradiator (Rad Source, Suwanee, GA) following SNBL USA SOPs.

Target Dose. 6.0 Gy (calculated Ld50/30 based on institutional lethality profile Target Dose Rate. Approximately 1.325 Gy/min Energy. 160 kV at 25 mA (on floor of RS-2000 chamber with circular RAD+)

Copper Filter Size. 0.3 mm Cu

Ion Chamber. RadCal 2086 Ion Chamber Dosimeter

Calculation. Dose (Gy)=Dose rate (Gy/min)*Time (min)

Test and Control Articles

Test Article. RYANODEX® (dantrolene sodium) for Injectable Suspension (Eagle Pharmaceutical, Inc.). Storage at room temperature (15 to 25° C.).

Control Article/Vehicle. Sterile Water for Injections (without bacteriostatic agent). Storage at room temperature (15 to 25° C.)

Preparation. Using aseptic procedure, each vial of test article was reconstituted by adding 5 mL of sterile water for injection (control article/vehicle) without bacteriostatic agent. The reconstituted suspension contained dantrolene sodium 250 mg/5 mL (50 mg/mL). The reconstituted vial was mixed by inversion to ensure an orange-colored uniform suspension. Prepared test article was maintained at room temperature (15 to 25° C.) and administered within 6 hours of reconstitution.

Test System

Species and Strain. C57BL/6 mice (*Mus musculus*). Naïve animals. Male. (Charles River Laboratories)

Body Weight Range. 20 to 30 g at start of acclimation

Age Range. 10 to 11 weeks at start of acclimation

Number of Animals for Acclimation. 120 males

Number of Animals for Dosing. 108 males

Animal Care

Housing. Animals were housed in a temperature- and humidity-controlled environment. The targeted range of temperature and relative humidity is between 20 and 26° C. and 30 and 70%, respectively. Excursions outside of the targeted humidity range for less than 4 hours were considered incidental and not reported. An automatic lighting system was set to provide a 12-hour light/dark cycle.

The animals were socially housed (no more than 3 per cage) in cages that comply with the Animal Welfare Act and recommendations set forth in the Guide for the Care and Use of Laboratory Animals (National Research Council 2011) and SNBL USA SOPs. Animals within an established group-housed unit were not introduced to a new social group during the study. Animals were singly housed during the study if they showed signs of aggression. Bedding and food were changed twice weekly and such that mice returned to clean cages after irradiation.

Diet and Feeding. Animals were offered PMI's LabDiet® Certified Rodent Diet 5002 ad libitum. The diet was routinely analyzed for contaminants and found to be within manufacturer's specifications. No contaminants are expected to be present at levels that would interfere with the outcome of the study. Food analysis records will be retained in the testing facility records. Starting on post irradiation Day 1, a portion of the diet was be placed onto the bottom of the cage.

Drinking Water. Acidified drinking water (pH 2.5 to 3.0) was prepared following SNBL USA SOPs and provided ad libitum to all animals. The source water is routinely analyzed for contaminants. No contaminants are expected to be present at levels that would interfere with the outcome of the study. Source water analysis records will be retained in the testing facility records.

Environmental Enrichment. Animals were given dietary supplements and cage enrichment devices throughout the course of the study per SNBL USA SOPs.

Veterinary Treatments. Veterinary assessments were conducted, but no veterinary treatments were administered to the animals. Morbidity were determined using the Irradiated Mouse Scoring Criteria SOP.

Experimental Design

Selection of Animals. Vendor supplied preventive health data was reviewed and approved by a veterinarian prior to receipt of animals. Upon receipt, animals were uncrated and examined by husbandry and research technicians. Animals noted with any clinical abnormalities were assessed by veterinary staff. One hundred ten (110) male C57BL/6 study mice were randomly assigned. Ten (10) spare male C57BL/6 mice were randomly assigned. Spare animals were returned to stock on or after Day 0.

Randomization. A stratified randomization scheme incorporating body weights were used to assign animals to study groups.

Acclimation Period. All animals were acclimated to the study room for a minimum of 14 days prior to irradiation. Acclimation phase data were collected from all animals, including spares. Assigned animals were replaced with spare animals as needed based on results generated during the acclimation phase. Spare animals were removed from the study on or after Day 0. Animals received acidified drinking water no later than the second day of acclimation.

Study Design. Animals were assigned to groups and treated as indicated in Table 1.

TABLE 1

Group Assignments

| | | | Dose | | Number of Animals | |
|---|---|---|---|---|---|---|
| | | | Level | Volume$^a$ | | |
| Group | Article | Schedule | (mg/kg) | (mL/kg) | Subset A | Subset B |
| 1 | Vehicle | SID Day 1 | 0 | 1 | $3^b + 10^c$ | $3^b + 10^c$ |
| 2 | Ryanodex | SID 1 hr prior to irradiation | 30 | 1 | $3^b + 10^c$ | $3^b + 10^c$ |
| 3 | | SID Day 1 | 30 | 1 | $3^b + 10^c$ | $3^b + 10^c$ |
| 4 | | SID Days 1-5 | 20 | 1 | $3^b + 10^c$ | $3^b + 10^c$ |
| 5 | | SID Day 1 | 30 | 1 | $1^d$ | $1^d$ |
| 6 | | SID Days 1-5 | 20 | 1 | $1^e$ | $1^e$ |

$^a$Total dose volume (mL) will be calculated based on the most recent body weight.
$^b$Interim necropsy, post irradiation Day 7
$^c$Terminal necropsy, post irradiation Day 30
$^d$Interim necropsy, post irradiation Day 2
$^e$Interim necropsy, post irradiation Day 6
SID: once per day Irradiation Preparation and Procedures Animal Restraint. Conscious animals were placed in a circular pie cage positioned on the floor of the RS-2000 chamber.

Irradiation Exposure Level and Dosimetry. Animals in Groups 1-4 were exposed to the calculated LD50/30 level of 6.0 Gy given by irradiation with the X-ray irradiator. Dose maps were created on each day of irradiation prior to irradiating animals and again after completed all irradiations of the day. Dose maps were archived with the study data.

Administration Frequency. Radiation were administered once to each animal in Groups 1-4 on Day 0 in the morning.

Administration of Test and Control Articles

Dose Level. 0, 20, or 30 mg/kg

Administration Route. All Groups were dosed by intravenous (IV) bolus injection into a tail vein or via temporary catheter into a tail vein followed by flushing with 0.2 mL of vehicle. The dose site, dose start time and dose volume were documented.

Administration Frequency. Test article were administered as described in In-text Table 1. Dose administrations were performed on Day 0 (Group 2, 1 hr prior to irradiation), Day 1 (Groups 1, 3 and 5), and Days 1-5 (Groups 4 and 6).

Administration Duration. As described in Table 1.

Observations and Examinations

Observational ARS Scoring. Scores for parameters of posture, coat, and behavior were performed and recorded per SNBL USA SOP once during acclimation (Day −1), once prior to irradiation on Day 0, twice daily on Days 1-29, and once on Day 30. On Days 1-29, the first ARS scoring started in the morning and the second ARS scoring started 4 to 6 hours following completion of the morning ARS scoring. Day 30 ARS scoring occurred in the morning, prior to necropsy. Based on the ARS Scoring SOP, if the sum of the three parameter scores total 8 or higher, starting 24 hours after last dose of test article, the animal was considered moribund and was handled per the moribund animal SOP. Animals having an ARS score of 8 or higher up to 24 hours after administration of test article were not considered moribund.

Mortality Checks. Cageside mortality checks were conducted per SOP, twice daily on Days 1-29, beginning 2-3 hours after completion of the respective morning and afternoon ARS scorings. Individual assessments were only documented for apparent moribund animals by re-scoring, or for found dead animals by removal. Additional mortality check were performed, as necessary.

Body Weight. Each animal was weighed twice during acclimation, once on Day 0 prior to irradiation, and every 3 days thereafter. Additional body weights were taken if necessary.

Blood Collection Procedures

TABLE 2

Specimen Collection

| | Hematology | |
|---|---|---|
| Group | Subset A | Subset B |
| 1 | 3 | 3 |
| 2 | 3 | 3 |
| 3 | 3 | 3 |
| 4 | 3 | 3 |

Blood Collection and Processing. Blood was collected at scheduled interim necropsy as described in Table 2.

Clinical Pathology

Hematology.
 Animals/Groups. The first 3 animals per subset for Groups 1-4.
 Minimum Sample Volume. 0.3 mL of blood
 Tube Type. 0.5 mL K2EDTA BD MAP tubes
 Method of Analysis. Hematology parameters were determined using an Advia automated analyzer. Hematology parameters were assessed at day 7 and day 30 post-irradiation.
 Parameters.
  White Blood Cells
  Red Blood Cells
  Hemoglobin
  Hematocrit
  Mean Corpuscular Volume
  Mean Corpuscular Hemoglobin
  Mean Corpuscular Hemoglobin Concentration
  Red Cell Distribution Width
  Platelets
  Mean Platelet Volume
  Differential leukocyte count (absolute)
   Neutrophils Absolute
   Lymphocytes Absolute
   Monocytes Absolute
   Eosinophils Absolute
   Basophils Absolute
  Reticulocyte Percent
  Reticulocyte Absolute Count
 Disposition. Residual EDTA-treated samples were stored up to 24 hours at 2 to 8° C. prior to analysis and discarded after analysis.

Terminal Procedures and Pathology

Scheduled Necropsy. On the day of necropsy, surviving animals in Groups 1-4 had terminal body weight recorded, and anesthesia performed per SNBL USA SOPs, followed by blood collected according to the methods described herein. Animals were euthanized by exsanguination and necropsied. Animals in Groups 5-6 were euthanized and discarded without necropsy.

Unscheduled Necropsy. Animals in Groups 1-4 approved for euthanasia had terminal body weight recorded, and anesthesia performed per SNBL USA SOPs. Animals were euthanized by exsanguination, if possible, and necropsied. Animals were euthanized and refrigerated prior to necropsy if necessary. Animals in Groups 5-6 approved for euthanasia were euthanized and discarded without necropsy.

Found Dead Animals. Found dead animals were weighed and necropsied within 24 hours. Animals were refrigerated prior to necropsy if necessary.

Gross Pathology. All animals were subjected to a full gross examination during necropsy. Two smears of femur bone marrow were collected from all scheduled and unscheduled animals. Bone marrow smears were not collected from animals that were found dead or animals that were refrigerated prior to necropsy. Examination of bone marrow smears, if required, was amended into the study protocols as necessary.

Organ Weights. Organ weights were only recorded from animals at scheduled necropsy. Relative organ weights were calculated as percentages of final body weight and brain weight. See Table 3 for list of tissues to be weighed.

Tissue Collection and Preservation. Tissues listed in Table 3 were collected from all animals and fixed for possible histopathologic examination. All tissues were fixed in 10% NBF, except for testes which were fixed in Modified Davidson's Fluid (MDF).

TABLE 3

Tissue Collections

| Tissues | Organ Weights | Tissue Collection and Preservation | Histopathologic Examination |
|---|---|---|---|
| Brain | ✓ | ✓ | — |
| Carcass | — | — | — |
| Gross lesions (if applicable) | — | ✓ | — |
| Intestine, cecum | — | ✓ | — |
| Intestine, colon | — | ✓ | — |
| Intestine, duodenum | — | ✓ | — |
| Intestine, ileum | — | ✓ | — |
| Intestine, jejunum | — | ✓ | — |
| Kidneys$^a$ | ✓ | ✓ | — |
| Liver | — | ✓ | ✓ |

TABLE 3-continued

Tissue Collections

| Tissues | Organ Weights | Tissue Collection and Preservation | Histopathologic Examination |
|---|---|---|---|
| Liver with gallbladder | ✓ | — | — |
| Spleen | ✓ | ✓ | — |
| Testes[a] | ✓ | ✓ | — |
| Thymus | ✓ | ✓ | — |

— = Not applicable

✓ = Applicable

[a]Organs will be collected, weighed, and/or examined as a pair

Reporting

Statistical Analyses. Summary statistics (mean and standard deviation) of all numerical data from scheduled animals was provided by SNBL USA. Calculations were performed using the full precision of the raw data. Data from time points where the number of scheduled animals as less than three per group was not statistically analyzed. Data from time points without scheduled control data were not statistically analyzed. Survival rate was calculated overall and for each dose group over the course of the study using the Kaplan-Meier estimator.

Results

Hematology parameters reached lowest values at 7 days after whole body irradiation, due to bone marrow suppression and blood cell toxicity. Recovery was assessed at 30 days post irradiation.

Overall, Ryanodex-treated animals lived longer than controls and showed improved absolute WBC, neutrophils, lymphocytes and platelet counts than non-treated animals. (See FIGS. 1-5).

Figure 6:
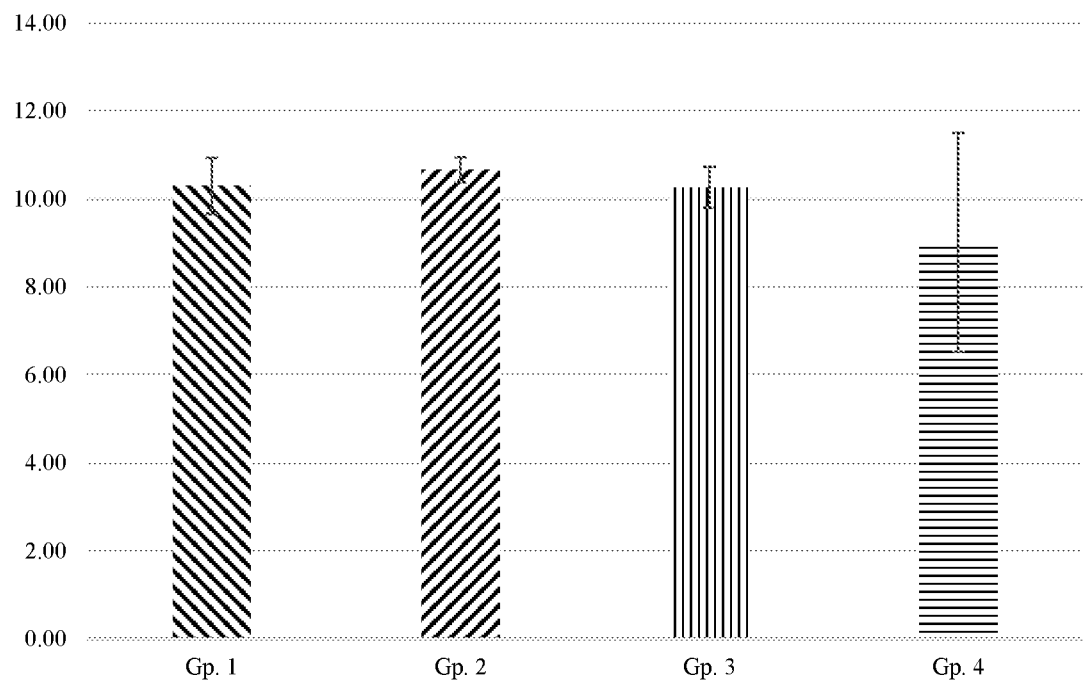
FIG. 6 is a series of histograms depicting a measure of hemoglobin (HgB) at day 7 and day 30 in Ryanodex-treated animals, groups 1-4. Groups 1: Control; 2: Ryanodex pre-irradiation; 3: Ryanodex post-irradiation single dose; and 4: Ryanodex post-irradiation multiple dose (days 1-5).
Figure 6:
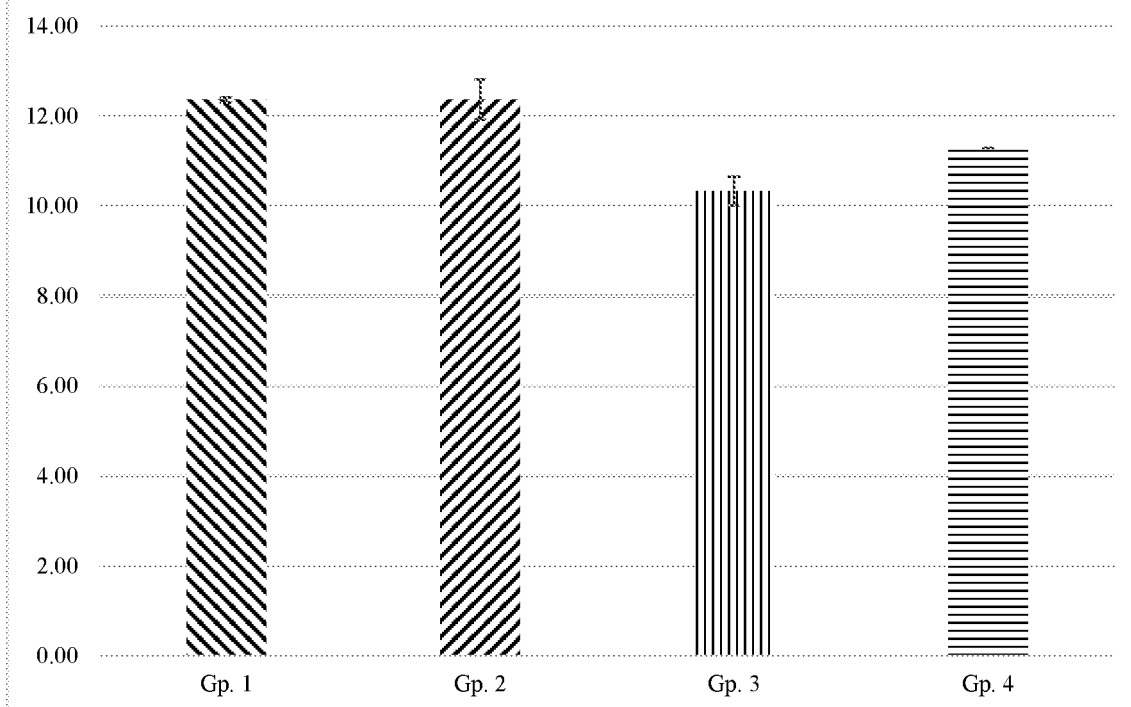
Figure 7:
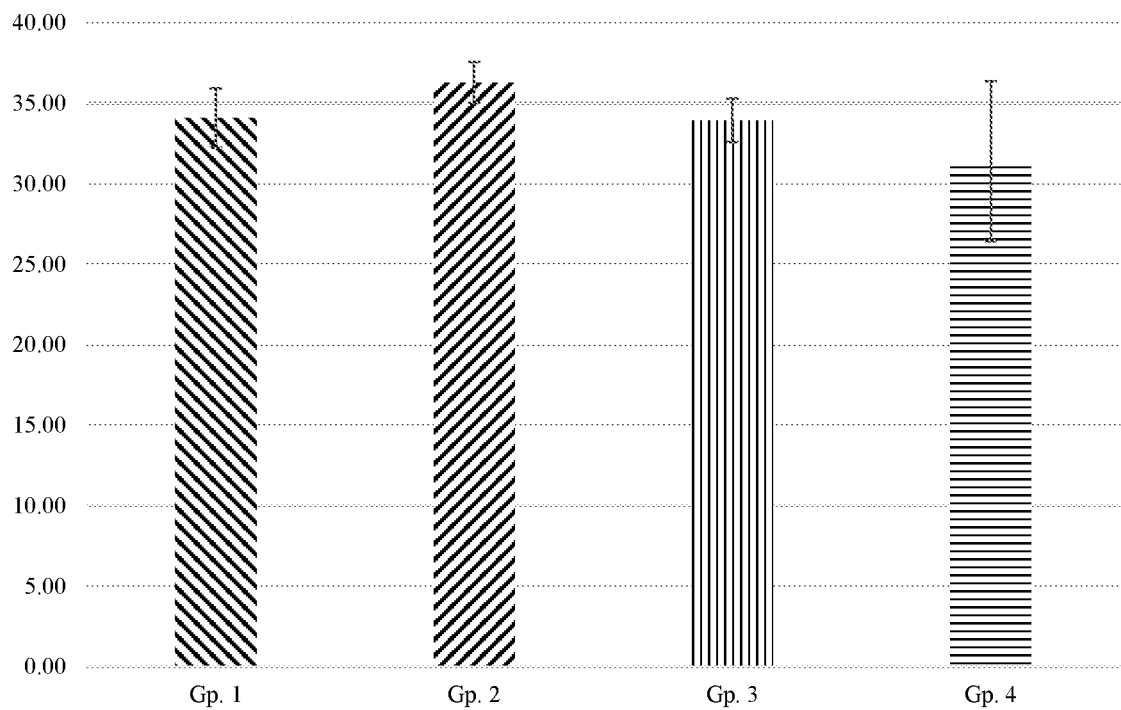
FIG. 7 is a series of histograms depicting a measure of hematocrit (HCT) at day 7 and day 30 in Ryanodex-treated animals, groups 1-4. Groups 1: Control; 2: Ryanodex pre-irradiation; 3: Ryanodex post-irradiation single dose; and 4: Ryanodex post-irradiation multiple dose (days 1-5).
Figure 7:
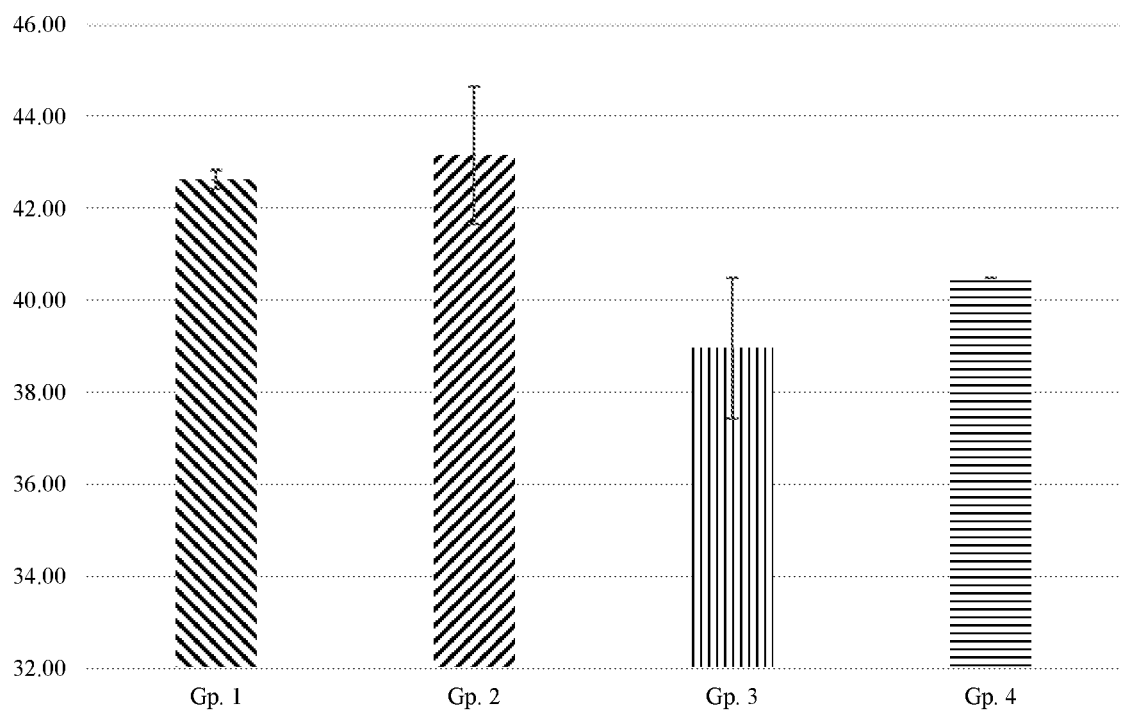

Also, as shown in FIGS. 6-7, measures of hemoglobin (HgB) and hematocrit (HCT) were taken at day 7 and day 30 in Ryanodex-treated animals.

Figure 8A:
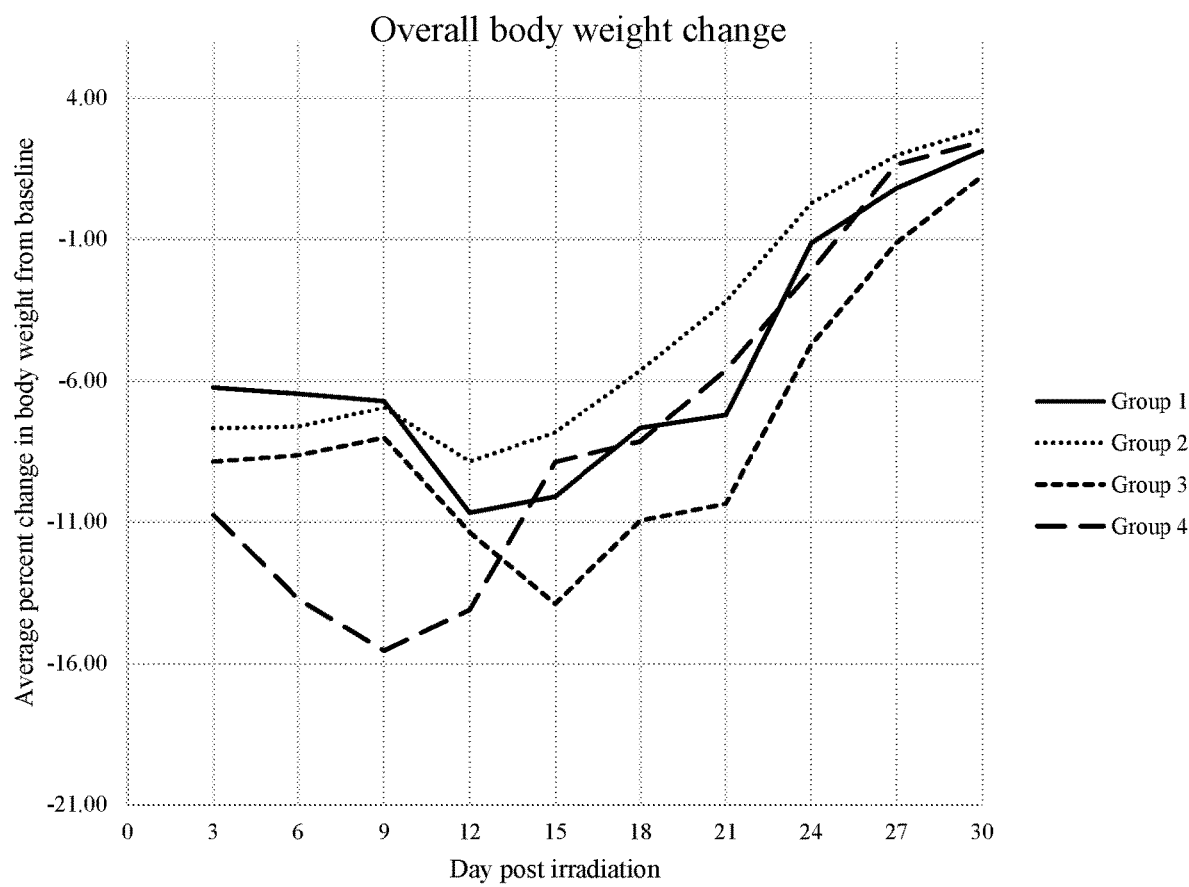
FIGS. 8A-8C are series of graphs depicting the average percent change in body weight from baseline from day 3 to day 30 post irradiation for groups 1-4.
Figure 8B:
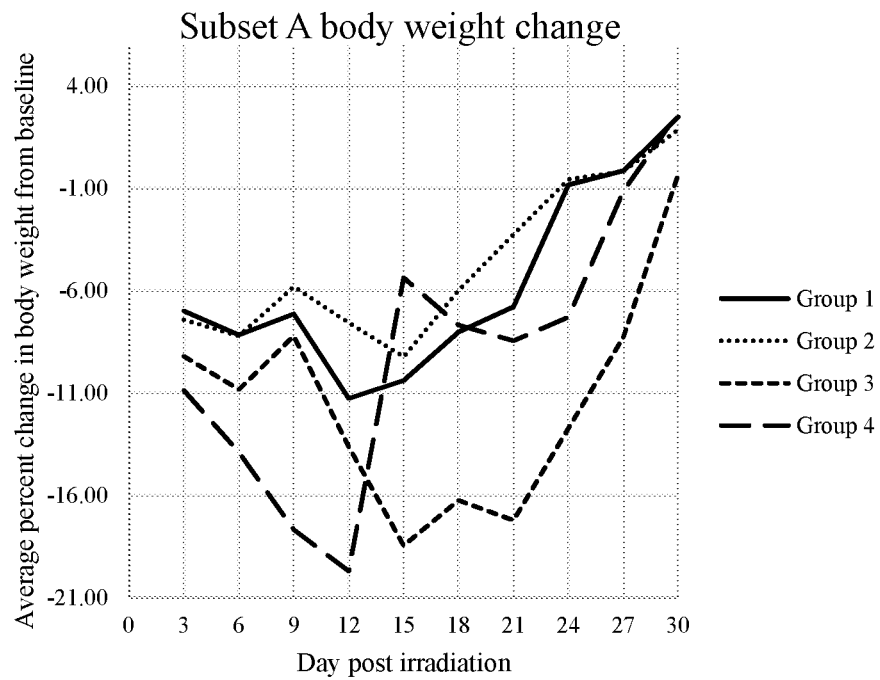
Figure 8C:
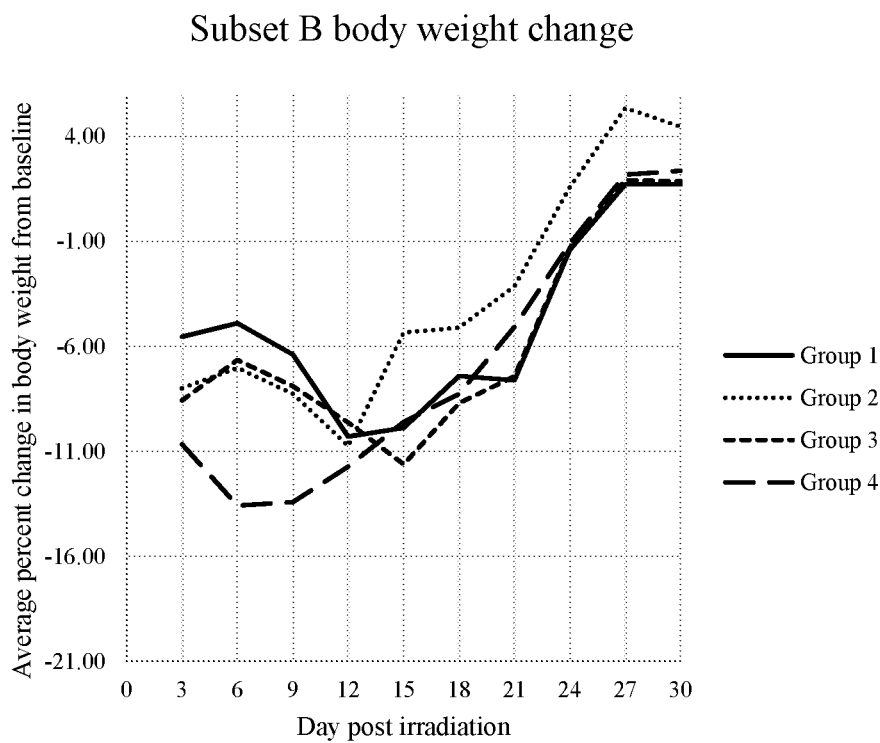

The average percent change in body weight was assessed from day 3 to day 30 post irradiation for animals treated with a control (e.g. sterile water); with Ryanodex pre-irradiation; with Ryanodex post-irradiation single dose; and with multiple dose of Ryanodex post-irradiation at days 1-5 (see FIGS. 8A-8C).

Figure 9A:
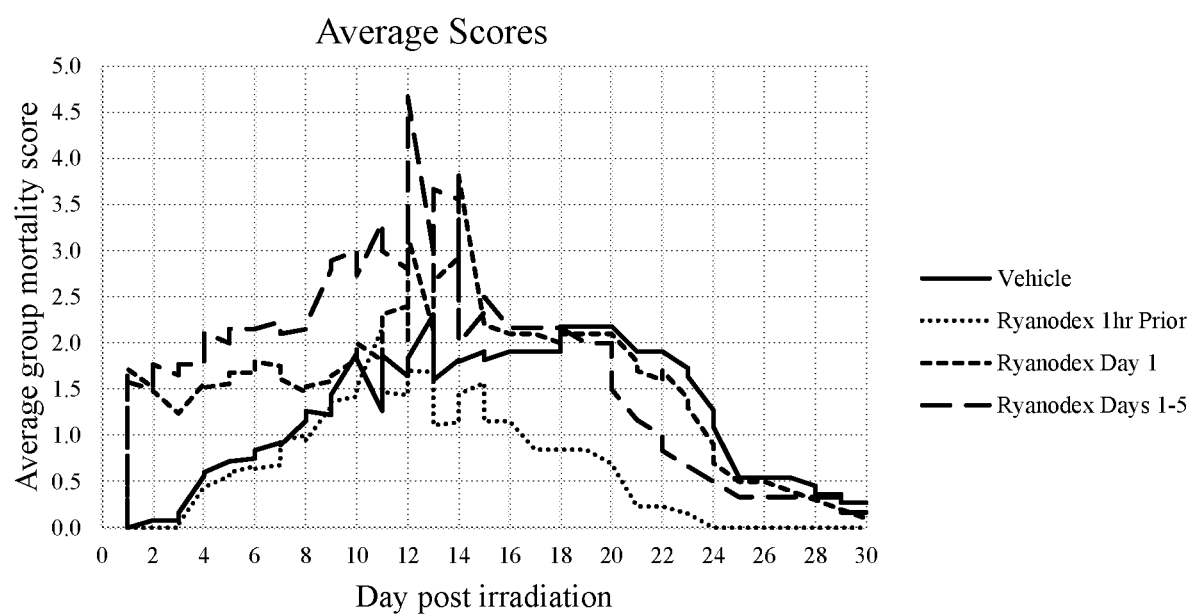
FIGS. 9A-9C are series of graphs depicting the average group mortality score from day 1 to day 30 post irradiation for animals treated with a control vehicle (sterile water), with Ryanodex 1 hr prior irradiation, with Ryanodex at day 1 post irradiation, and with Ryanodex at days 1-5 post irradiation.
Figure 9B:
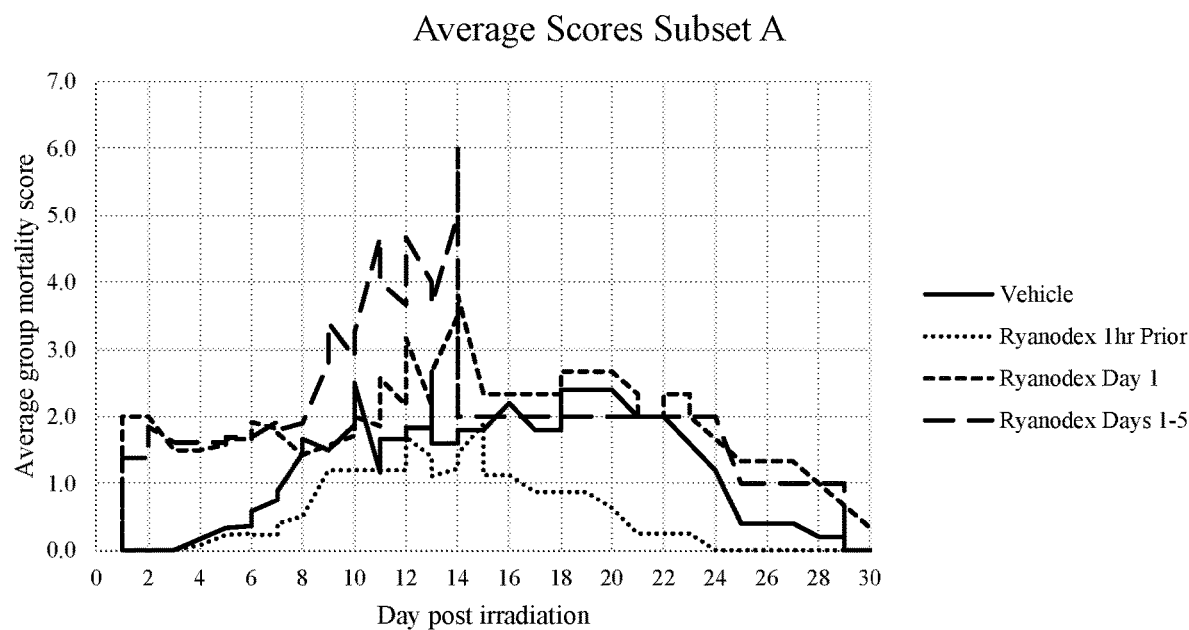
Figure 9C:
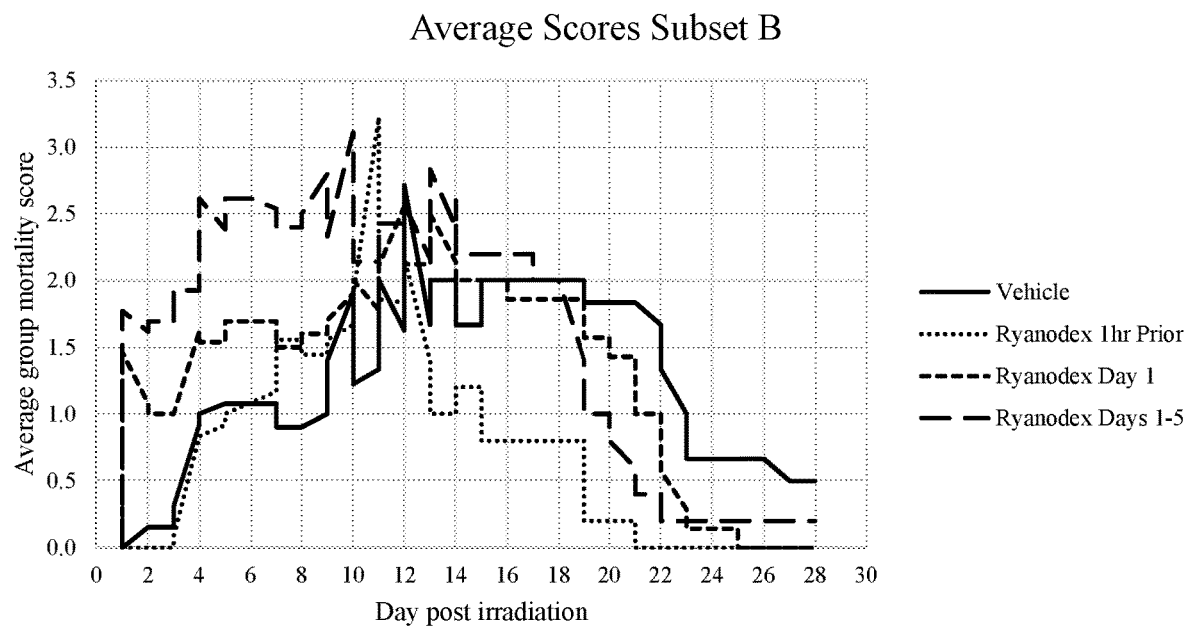

The average group mortality score was assessed from day 1 to day 30 post irradiation for animals treated with a control vehicle (sterile water), with Ryanodex 1 hr prior irradiation, with Ryanodex at day 1 post irradiation, and with Ryanodex at days 1-5 post irradiation. See FIGS. 9A-9C.

Example 2

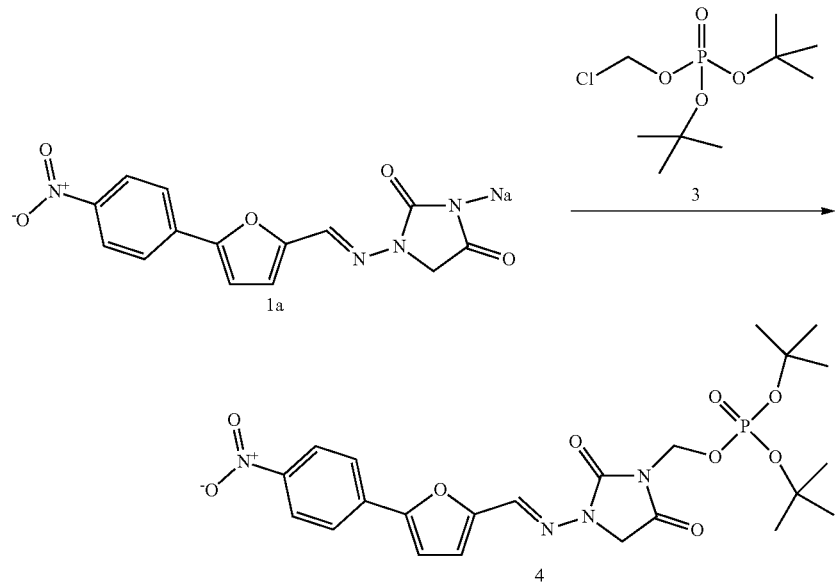

Sodium dantrolene (1 eq.) was dissolved in anhydrous dimethylformamide. Reagent 3 (1 eq) was added and the reaction mixture was stirred at 60° C. under nitrogen. After 4 h, another equivalent of reagent 3 was added and the reaction was stirred at 60° C. overnight. Then the reaction was diluted with ethyl acetate and washed twice with saturated sodium chloride. The layers were separated. The organic layers were dried over sodium sulfate and concentrated in vacuo. The crude product was purified using silica gel chromatography. The desired product was isolated in 90-95% purity. $^1$H NMR was consistent with that predicted for the desired product.

Example 2, Method A: 1a was dried with $P_2O_5$ overnight. To a mixture of 1a (500 mg, 1.48 mmol) in DMF (10 mL) was added 3 (0.84 mL, 3.72 mmol) followed by NaI (245 mg, 1.63 mmol) at 0° C. The resultant mixture was stirred at room temperature for 64 h. The mixture was diluted with EtOAc (30 mL) and brine (20 mL). The organic layer was separated, washed with water (2×15 mL), dried over anhydrous $Na_2SO_4$, filtered, and evaporated. The crude residue was purified by flash chromatography (twice), eluting with 0-10% MeOH/$CH_2Cl_2$ to afford the desired compound 4 (355 mg, 45%) as a yellow solid.

Example 2, Method B: 1a was dried with P$_2$O$_5$ overnight. To a mixture of 1a (8.0 g, 23.8 mmol) in DMF (160 mL) was added 3 (6.5 mL, 28.79 mmol) followed by NaI (4.28 g, 28.55 mmol) at room temperature. The resultant mixture was stirred at room temperature for 40 h. The mixture was diluted with EtOAc (250 mL) and brine (60 mL). The organic layer was separated, washed with water (2×75 mL), dried over anhydrous Na$_2$SO$_4$, filtered, and evaporated. The residue was triturated with CH$_2$Cl$_2$-hexanes to give a yellow solid (~7 g). This solid was purified by flash chromatography (twice, deactivated SiO$_2$), eluting with 0-10% MeOH/CH$_2$Cl$_2$ to afford the desired compound 4 (1.92 g, 15%) as a yellow solid.

Example 3

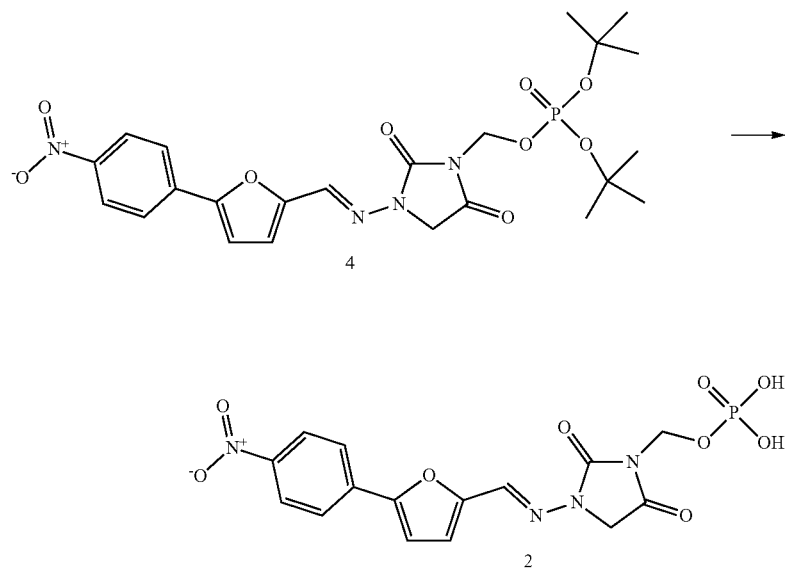

Example 4

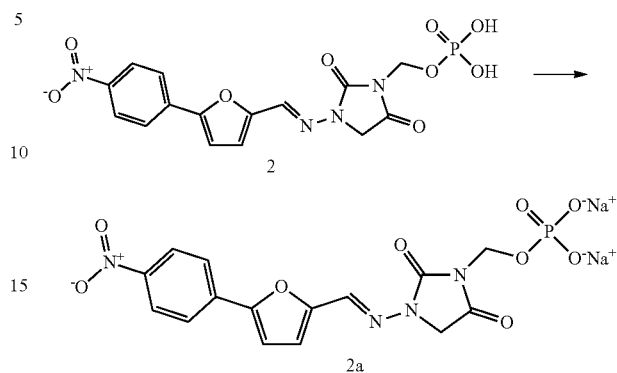

A sample of compound 4 was treated with 1 ml of 9/1 mixture of trifluoroacetic acid/water for 20-30 min at ambient temperature. The excess TFA was removed immediately using high vacuum and the resulting solid was collected by filtration, washed with water (5 ml) and air dried. The starting material, reaction mixture and final product were analyzed by LC/MS to determine if 2 reverts to dantrolene during the deprotection conditions. No reversion of 2 to dantrolene was observed. The $^1$H NMR of the product was consistent with that predicted for the desired product.

Example 3, Method A: To a mixture of 4 (886 mg, 1.65 mmol) in CH$_2$Cl$_2$ (9 mL) was added TFA (9 mL). The resultant mixture was stirred at room temperature for 3 h. The solvent was evaporated on a rotary evaporator to dryness. The resulting residue was triturated with hexanes for 1 h and the yellow solid was filtered and dried to yield the desired compound 2 (660 mg, 94%).

50 mg of 2 was mixed with 3 ml methanol (complete dissolution) and applied to 1 g of Na+ ion exchange column. The compound was eluted with methanol and after lyophilization gave 18 mg (36% recovery) of an orange solid. This material was dissolved in water and carefully titrated to pH 8.5 by the addition of small aliquots of 0.1 M NaOH, with stirring. The solution was then lyophilized to yield the orange solid, compound 2a. LC/MS of the sample before and after lyophilization was identical, which indicated no reversion to dantrolene occurred during the ion exchange. $^1$H NMR of the product was consistent with that predicted for the desired product.

Example 4, Method A: To a stirred suspension of 2 (500 mg, 1.17 mmol) in water (63 mL, HPLC grade) was added 0.1 N NaOH (23.6 mL, 2.34 mmol) at room temperature in 650 μL aliquots immediately followed by a quick vortex until the pH reached 8.5. The solution was filtered, and the filtrate was lyophilized overnight to give the title compound 2a (530 mg, 96%) as a yellow solid. MS (CI) m/z=424.9 [M]$^+$. $^1$H NMR (300 MHz, D$_2$O): δ 8.08 (d, J=8.8 Hz, 2H), 7.72 (d, J=8.8 Hz, 2H), 7.59 (s, 1H), 6.98 (d, J=3.6 Hz, 1H), 6.86 (d, J=3.6 Hz, 1H), 5.19 (d, J=6.0 Hz, 2H), 4.32 (s, 2H).

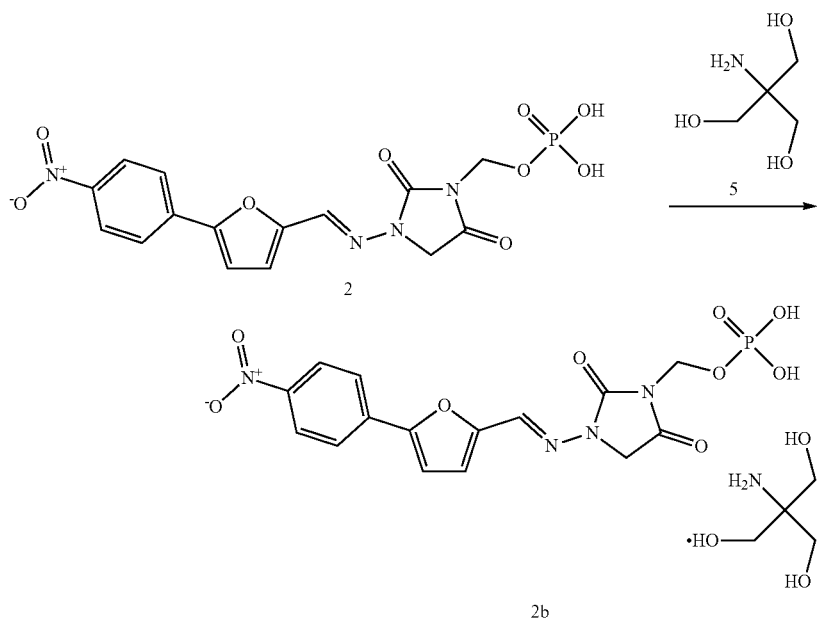

To a stirred suspension of 2 (100 mg, 0.23 mmol) in water (12 mL, HPLC grade) was added Tris (5, 57 mg, 0.47 mmol) dissolved in water (5 mL) dropwise at room temperature. The pH of the final solution was 6.6. The solution was filtered, and the filtrate was lyophilized overnight to give the title compound 2b (150 mg, 95%) as a yellow solid. MS (CI) m/z=424.9 [M]+. $^1$H NMR (300 MHz, DMSO-$d_6$): δ 8.24 (m, 2H), 7.93 (m, 2H), 7.73 (m, 1H), 7.12 (m, 1H), 6.97 (m, 1H), 5.20 (m, 2H), 4.40 (m, 2H), 3.63 (m, 15H).

Example 6

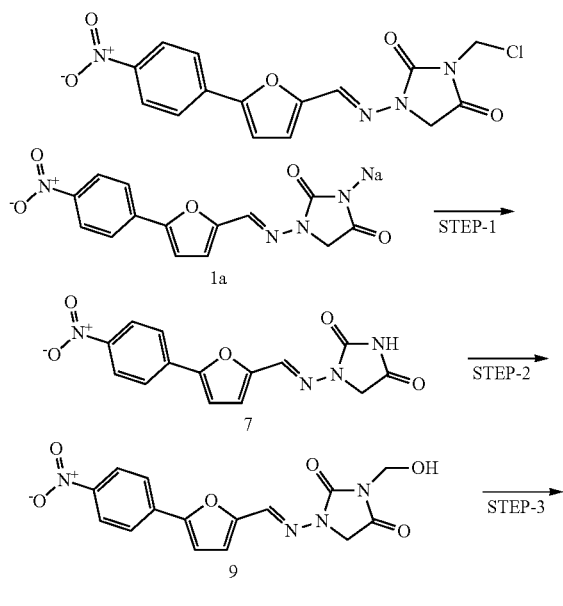

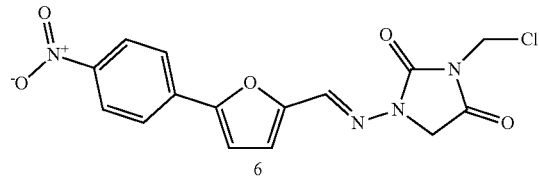

STEP 1: 1a was dried with $P_2O_5$ overnight. To a mixture of 1a (1.0 g, 2.97 mmol) in DMF (20 mL) was added glacial acetic acid (340 μL, 5.95 mmol) at room temperature. The mixture was stirred overnight at room temperature. The mixture was poured onto crushed ice, the solid was filtered and washed with water. The resultant wet solid was dried over anhydrous $P_2O_5$ overnight to get the desired compound 7 (920 mg, 98%) as a yellow solid.

STEP 2: To a suspension of 7 (1.35 g, 4.29 mmol) in water (45 mL) was added formalin (4.35 mL, 57.45 mmol, 37% formaldehyde in water) followed by $K_2CO_3$ (51 mg, 0.37 mmol). The mixture was stirred at room temperature for 24 h. The reaction mixture was filtered, and the yellow solid was washed with 3% aqueous formaldehyde and air dried for 24 h to give the desired compound 9 (1.2 g, 82%).

STEP 3: To a solution of 9 (615 mg, 1.78 mmol) in DMF:Acetone (40 mL, 15:25 mL) was added $PCl_3$ (1.2 mL, 13.71 mmol) slowly at 0° C. The reaction mixture was stirred for 10 min at 0° C.; and 2 h at room temperature. Then the mixture was poured onto crushed ice, and the resulting yellow solid was filtered, washed with water (3×50 mL) and dried over $P_2O_5$ under vacuo for 16 h to give the desired compound 6 (600 mg, 92%). $^1$H NMR (300 MHz, DMSO-$d_6$): δ 8.33 (d, J=8.5 Hz, 2H), 8.03 (d, J=8.8 Hz, 2H), 7.87 (s, 1H), 7.48 (d, J=3.3 Hz, 1H), 7.11 (d, J=3.6 Hz, 1H), 5.42 (s, 2H), 4.53 (s, 2H).

Example 7

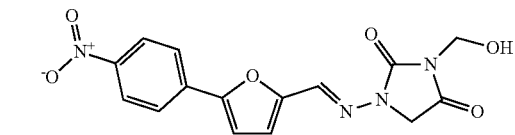

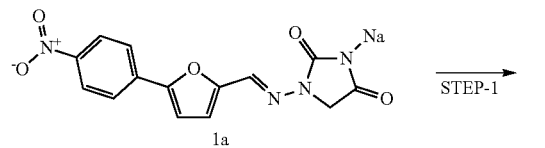

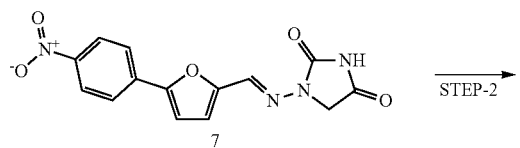

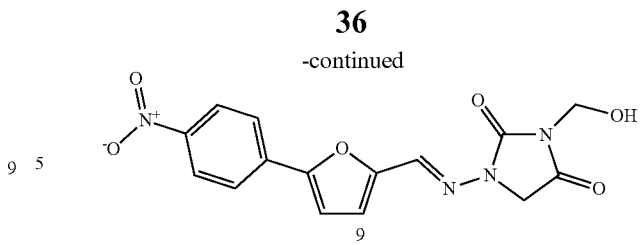

STEP 1: 1a was dried with $P_2O_5$ overnight. To a mixture of 1a (1.0 g, 2.97 mmol) in DMF (20 mL) was added glacial acetic acid (340 μL, 5.95 mmol) at room temperature. The reaction mixture was stirred overnight at room temperature. The mixture was poured onto crushed ice, the resulting solid was filtered and washed with water. The wet solid was dried over anhydrous $P_2O_5$ overnight to get the desired compound 7 (920 mg, 98%) as a yellow solid.

STEP 2: To a suspension of 7 (90 mg, 0.28 mmol) in water (2.6 mL) was added formalin (0.29 mL, 3.83 mmol, 37% formaldehyde in water) followed by $K_2CO_3$ (3.4 mg, 0.02 mmol). The mixture was stirred at room temperature for 24 h. The reaction mixture was filtered, and the yellow solid was washed with 3% aqueous formaldehyde and air dried for 24 h to give the desired compound 9 (86 mg, 88%). MS (CI) m/z=343 [M]$^+$. $^1$H NMR (300 MHz, DMSO-$d_6$): δ 8.32 (d, J=9.0 Hz, 2H), 8.03 (d, J=9.1 Hz, 2H), 7.83 (s, 1H), 7.47 (d, J=3.6 Hz, 1H), 7.08 (d, J=3.6 Hz, 1H), 6.52 (t, 1H), 4.85 (d, J=7.1 Hz, 2H), 4.45 (s, 2H).

Example 8

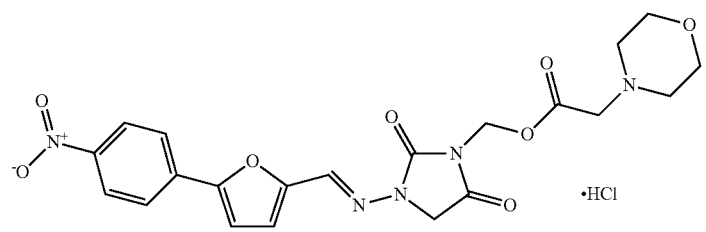

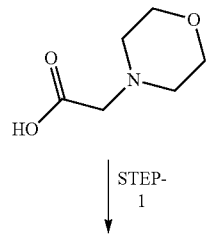

STEP-1

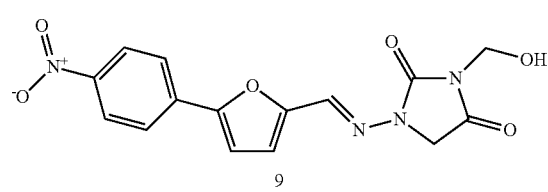

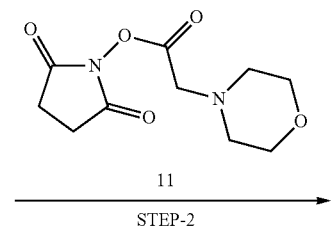

STEP-2

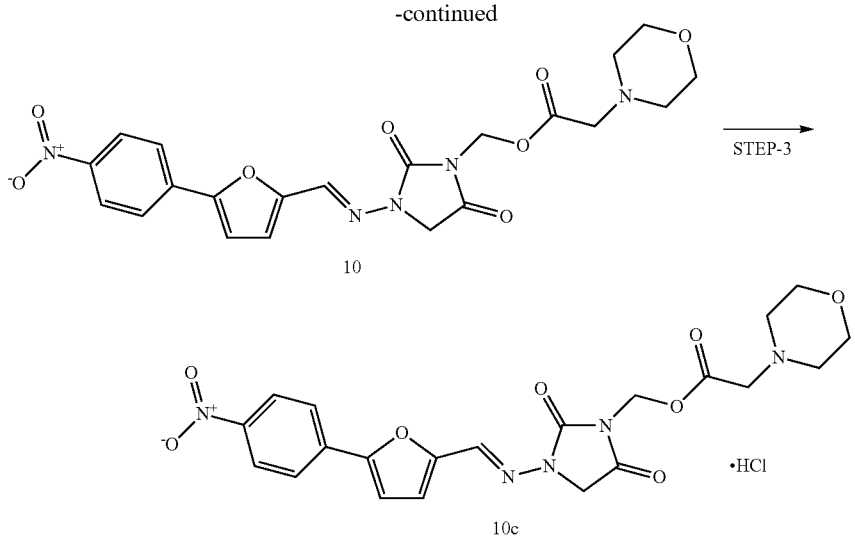

10

10c

STEP 1: Anhydrous DMF (0.8 mL, 10.33 mmol) was dissolved in anhydrous tetrahydrofuran (13 mL). This solution was added dropwise to a stirred solution of thionyl chloride (0.75 mL, 10.33 mmol) dissolved in tetrahydrofuran (9 mL) and cooled in an ice bath. After complete addition and 30 minutes on ice, the ice bath was removed and solid N-hydroxysuccinimide (832 mg, 7.23 mmol) was added (which completely dissolved) immediately followed by addition of solid pre-powdered morpholine acetic acid (1.0 g, 6.88 mmol). The morpholine acetic acid dissolved slowly giving a homogeneous solution that rapidly became cloudy. The reaction was left vigorously stirring overnight at room temperature. The white solid was washed with tetrahydrofuran and dried under vacuum, to yield the desired compound 11 (1.6 g, 96%) as a white solid.

STEP 2: To a solution of 9 (660 mg, 1.92 mmol) and 11 (928 mg, 3.83 mmol) in anhydrous DMF (12 mL) was added triethylamine (0.39 mL, 2.8 mmol). The resulting mixture was stirred overnight at 60° C. The reaction mixture was cooled to room temperature and purified by reverse phase column chromatography using acetonitrile-water as eluent. The column fractions were analyzed by HPLC and the fractions containing product were lyophilized to get the crude compound with 50% purity. This crude product was again purified by preparative HPLC using acetonitrile-water. The lyophilization of pure fractions gave the title compound 10 (100 mg, 10%) as a yellow solid.

STEP 3: To a stirred solution of 10 (75 mg, 0.16 mmol) in anhydrous 1,4-dixoane (4 mL) was added HCl (0.3 mL, 4N in 1,4-Dioxane) at room temperature and the resultant mixture stirred for 2 h. The solvents were evaporated on a rotary evaporator to dryness. The resulting residue was dissolved in water and lyophilized overnight to yield 10c (75 mg, 94%).

MS (CI) m/z=472.1 [M]$^+$. $^1$H NMR (300 MHz, DMSO-d$_6$): δ 8.33 (d, J=8.8 Hz, 2H), 8.03 (d, J=9.1 Hz, 2H), 7.89 (s, 1H), 7.49 (d, J=3.6 Hz, 1H), 7.11 (d, J=4.1 Hz, 1H), 5.60 (s, 2H), 4.54 (s, 2H), 3.32-3.81 (m, 10H). $^1$H NMR (300 MHz, D$_2$O): δ 8.17 (d, J=8.5 Hz, 2H), 7.81 (d, J=8.8 Hz, 2H), 7.60 (s, 1H), 6.93-7.02 (m, 1H), 6.88-6.92 (m, 1H), 5.73 (s, 2H), 4.39 (s, 2H), 4.26 (s, 2H), 3.90-4.09 (m, 4H), 3.30-3.52 (m, 4H).

Example 9

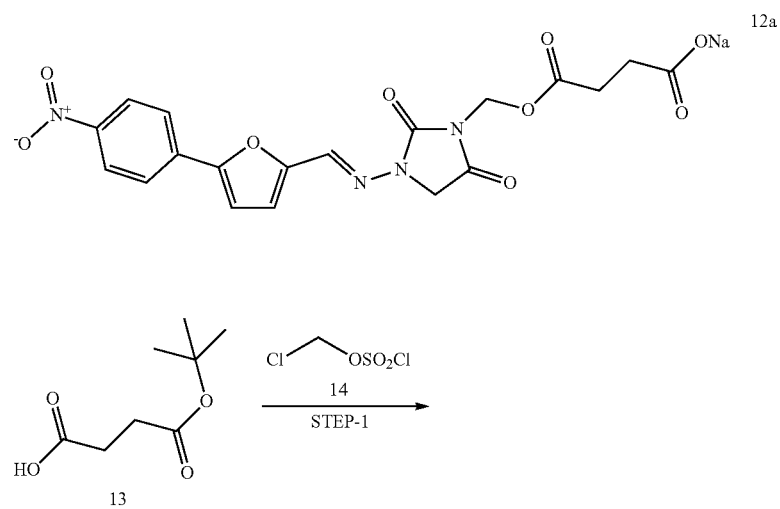

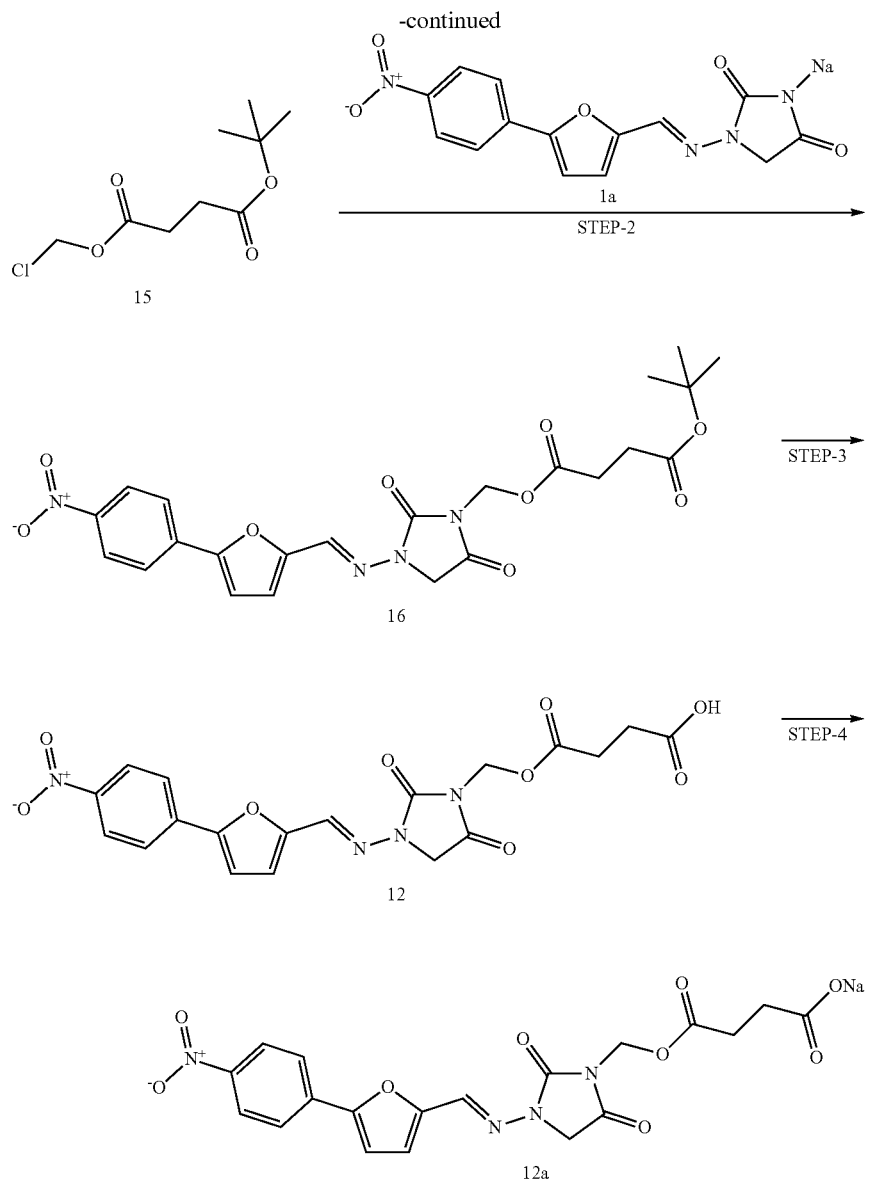

STEP 1: To a mixture of K₂CO₃ (4.0 g, 28.94 mmol) and TBAHSO₄ (240 mg, 0.70 mmol) in water (8 mL) was added 13 (2.0 g, 11.48 mmol) in CH₂Cl₂ (8 mL) at 0° C. The resultant mixture was stirred for 20 min at 0° C.; before adding 14 (1.3 mL, 12.85 mmol) and again stirred for 3 h. The organic layer was separated and washed with water (2×5 mL) and saturated aqueous brine (5 mL), The CH₂Cl₂ layer was dried over anhydrous Na₂SO₄, filtered and concentrated in vacuo. The crude residue was purified by flash chromatography eluting with 0-100% EtOAc/hexanes to get the desired compound 15 (2.2 g, 86%) as a colorless gum.

STEP 2: 1a was dried with P₂O₅ overnight. To a mixture of 15 (2.2 g, 9.87 mmol) in DMF (35 mL) was added 1a (1.66 g, 4.93 mmol) at room temperature. The resultant mixture was stirred at room temperature for 20 h. The mixture was diluted with EtOAc (50 mL) and washed with water (2×25 mL) and saturated aqueous brine (15 mL). The EtOAc layer was dried over anhydrous Na₂SO₄, filtered, and evaporated under vacuo. The crude residue was purified by flash chromatography eluting with 0-100% EtOAc/CH₂Cl₂ (twice) followed by trituration with CH₂Cl₂-hexanes to get the desired compound 16 (500 mg, 20%) as a yellow solid.

STEP 3: To a mixture of 16 (340 mg, 0.68 mmol) in CH₂Cl₂ (18 mL) was added TFA (1.8 mL). The resultant mixture was stirred overnight at room temperature. The solvents were evaporated on a rotary evaporator to dryness. The resulting residue was triturated with hexanes for 1 h and the yellow solid was filtered and dried to yield the desired compound 12 (300 mg, 99%).

STEP 4: To a stirred suspension of 6 (260 mg, 0.58 mmol) in water (36 mL, HPLC grade) was added 0.1 N NaOH (5.85 mL, 0.58 mmol) at room temperature in 400 μL aliquots immediately followed by a quick vortex. The pH of the final solution was 6.73. The solution was filtered, and the filtrate was lyophilized overnight to give the title compound 12a (150 mg, 55%) as a yellow solid. MS (CI) m/z=445.1 [M]⁺.
¹H NMR (300 MHz, DMSO-d₆): δ 8.34 (d, J=8.8 Hz, 2H), 8.04 (d, J=8.8 Hz, 2H), 7.87 (s, 1H), 7.49 (d, J=3.6 Hz, 1H), 7.11 (d, J=3.8 Hz, 1H), 5.43 (s, 2H), 4.51 (s, 2H), 2.40 (m, 2H), 2.15 (m, 2H).

Example 10
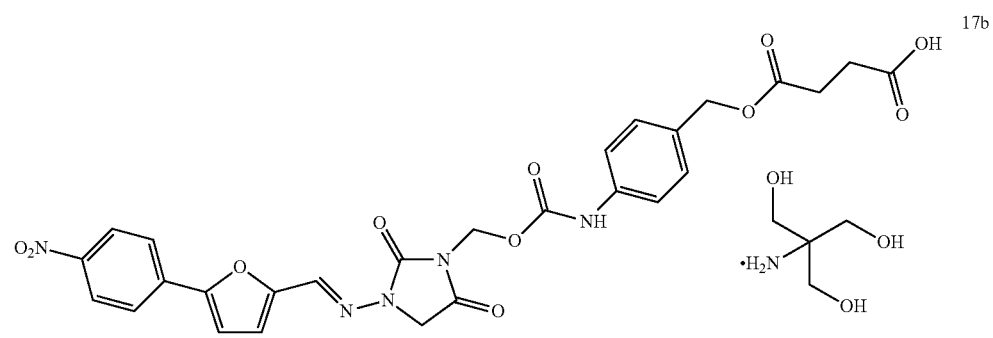
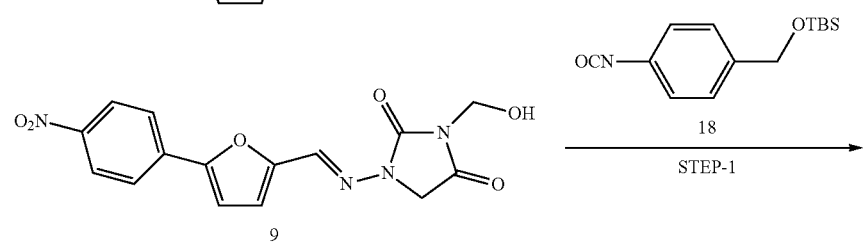
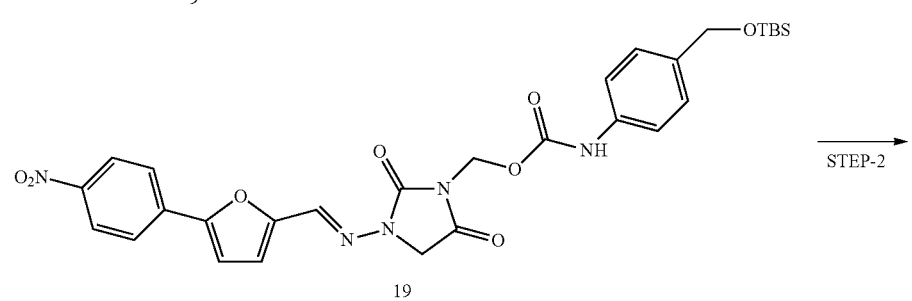
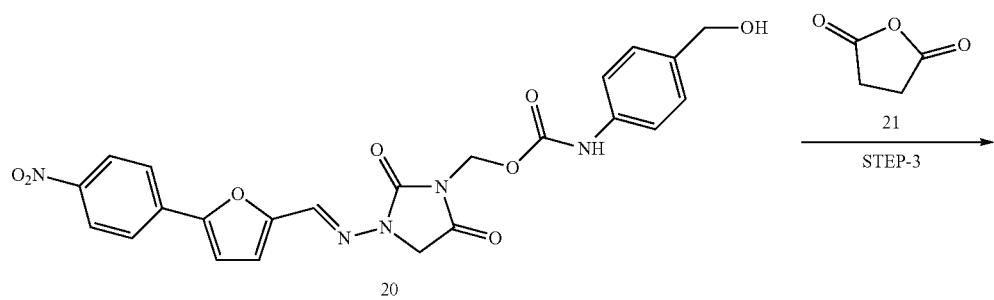
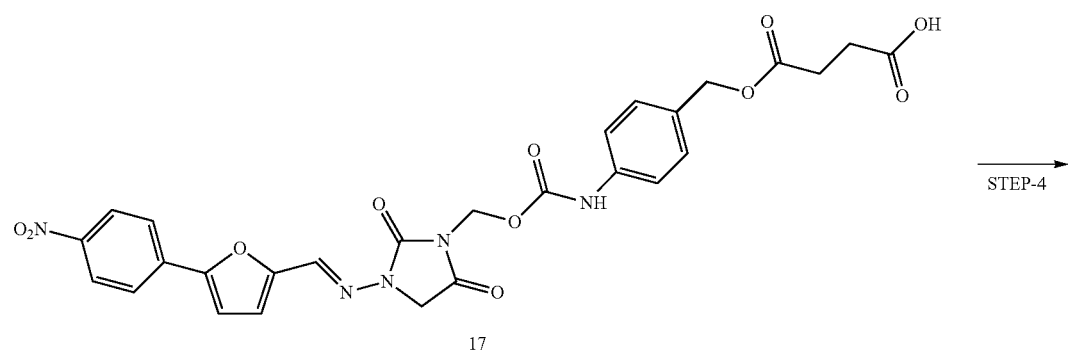

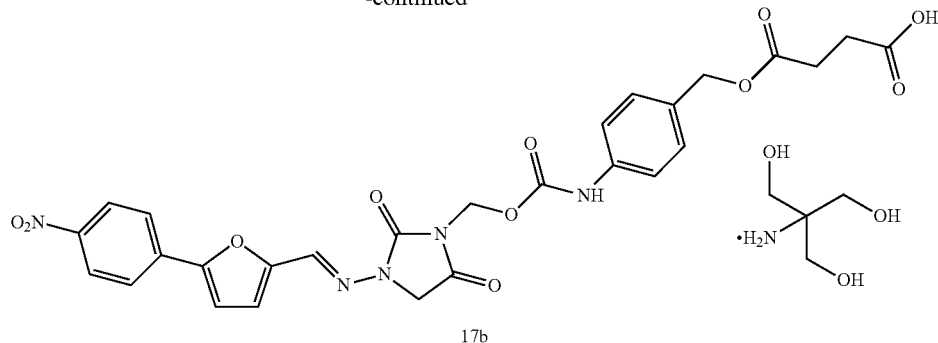

17b

STEP 1: To a solution of compound 9 (500 mg, 1.45 mmol) in anhydrous DMF (10 mL) was added compound 18 (488 mg, 1.85 mmol) in DMF (2 mL) followed by TEA (0.3 mL, 2.2 mmol). The resultant mixture was stirred for 16 h at room temperature. The mixture was diluted with EtOAc (50 mL), washed with water (2×15 mL). The organic layer was dried over anhydrous $Na_2SO_4$, filtered and evaporated to dryness. The crude product was purified twice by flash chromatography eluting with 0-10% MeOH/$CH_2Cl_2$ to obtain the desired compound 19 (350 g, 40%) as a yellow solid.

STEP 2: To a solution of compound 19 (200 mg, 0.32 mmol) in MeOH:1,4-Dioxane (1:1, 6 mL) was added p-toluenesulfonic acid monohydrate (63 mg, 0.32 mmol). The clear solution was stirred for 16 h at room temperature. The solvents were evaporated on a rotary evaporator to dryness. The residue was purified by flash chromatography eluting with 0-10% MeOH/$CH_2Cl_2$ to obtain the desired compound 20 (125 g, 77%) as a yellow solid.

STEP 3: To a solution of compound 20 (120 mg, 0.24 mmol) and compound 21 (26.4 mg, 0.26 mmol) in m-xylene: 1,4-dioxane (1:1, 16 mL) was added p-toluenesulfonic acid monohydrate (15 mg, 0.07 mmol) and 4 Å molecular sieves (100 mg). The resultant mixture was refluxed for 16 h. The reaction mixture was cooled to room temperature, diluted with 1,4-dioxane (30 mL) and filtered. The filtrate was evaporated, and the crude residue was purified twice by flash chromatography eluting with 0-10% MeOH/$CH_2Cl_2$ to get the desired compound 17 (16 mg, 11%) as a yellow solid.

STEP 4: To a stirred suspension of 17 (5 mg, 8.4 μmol) in water (3 mL, HPLC grade) was added 0.1 N Tris (90 μL, 8.9 μmol) dropwise at room temperature. The mixture was stirred at room temperature for 3 h. The solution was filtered, and the filtrate was lyophilized overnight to give the title compound 17b (6 mg, 100%) as a yellow solid. MS (CI) m/z=594.1 [M]+. $^1$H NMR (300 MHz, DMSO-$d_6$): δ 9.96 (brs, 1H), 8.34 (d, J=8.8 Hz, 2H), 8.05 (d, J=8.5 Hz, 2H), 7.89 (s, 1H), 7.5 (d, J=3.2 Hz, 1H), 7.46 (d, J=8.8 Hz, 2H), 7.29 (d, J=8.5 Hz, 2H), 7.12 (d, J=3.5 Hz, 1H), 5.57 (s, 2H), 4.99 (s, 2H), 4.55 (s, 2H), 3.23-3.32 (m, 9H), 2.33-2.36 (m, 4H).

Example 11

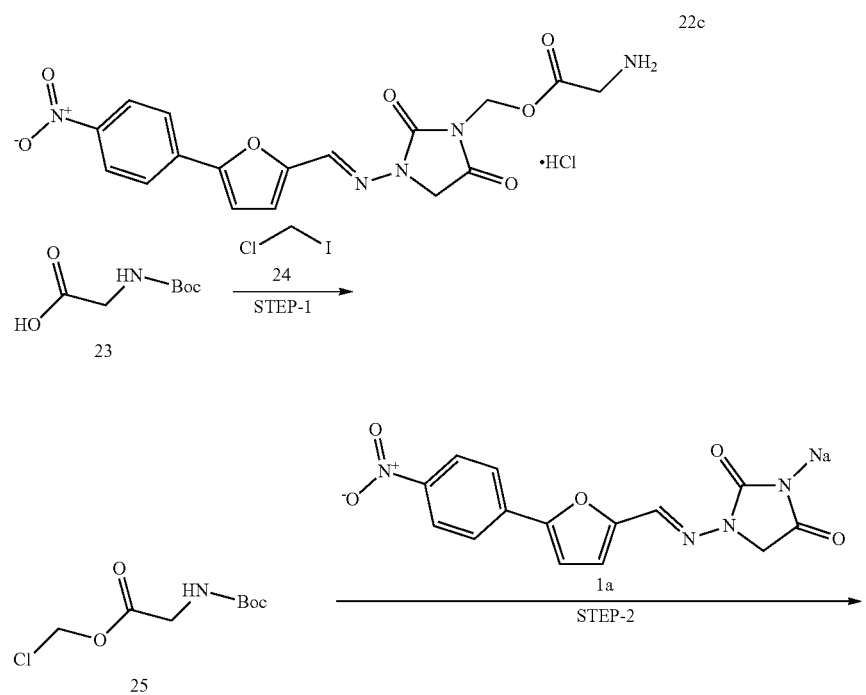

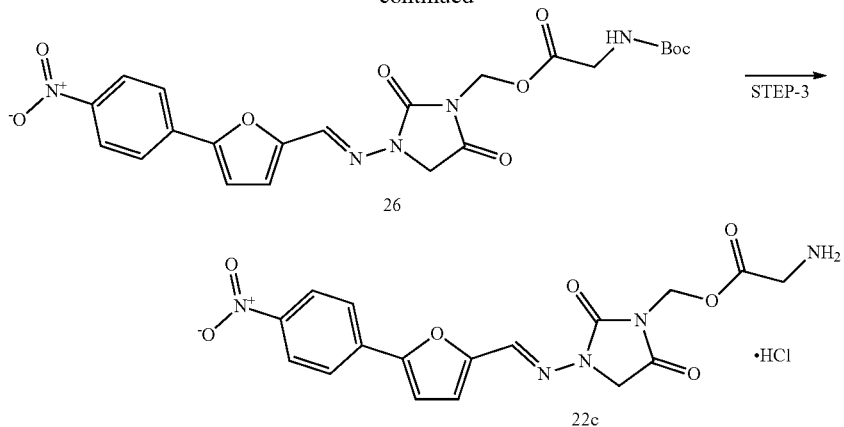

STEP 1: To a mixture of 23 (2.5 g, 14.28 mmol) in DMF (30 mL) was added triethylamine (3.47 mL, 24.93 mmol) followed by 24 (3.92 mL, 53.9 mmol) at room temperature. The resultant mixture was stirred at room temperature for 40 h. The mixture was diluted with EtOAc (100 mL) and water (50 mL). The EtOAc layer was washed with water (2×25 mL), 5% NaHCO$_3$ (25 mL), and saturated aqueous brine (15 mL). The EtOAc layer was dried over anhydrous Na$_2$SO$_4$ and concentrated in vacuo. The crude residue was purified by flash chromatography eluting with 0-100% EtOAc/hexanes to get the desired compound 25 (657 mg, 21%) as a colorless oil.

STEP 2: 1a was dried with P$_2$O$_5$ overnight. To a mixture of 1a (647 mg, 1.92 mmol) in DMF (12 mL) was added 25 (647 mg, 2.89 mmol) at room temperature. The resultant mixture was stirred at room temperature for 110 h. The mixture was diluted with EtOAc (40 mL), washed with water (2×15 mL), and saturated aqueous brine (15 mL). The EtOAc layer was dried over anhydrous Na$_2$SO$_4$, filtered, and evaporated under vacuo. The crude residue was purified by flash chromatography eluting with 0-100% EtOAc/CH$_2$Cl$_2$ to get the desired compound 26 (260 mg, 27%) as a yellow solid.

STEP 3: To a stirred solution of 26 (210 mg, 0.41 mmol) in anhydrous 1,4-dixoane (4 mL) was added HCl (4 mL, 4N in 1,4-Dioxane) at room temperature and the resultant mixture was stirred overnight. The solvents were evaporated on a rotary evaporator to dryness. The resulting residue was triturated with hexanes for 1 h and the yellow solid was filtered and dried to yield the title compound 22c (153 mg, 83%). MS (CI) m/z=402.1 [M]$^+$. $^1$H NMR (300 MHz, DMSO-d$_6$): δ 8.47 (brs, 3H), 8.34 (d, J=8.8 Hz, 2H), 8.04 (d, J=8.8 Hz, 2H), 7.91 (s, 1H), 7.50 (d, J=3.6 Hz, 1H), 7.12 (d, J=3.6 Hz, 1H), 5.61 (s, 2H), 4.56 (s, 2H), 3.85 (s, 2H).

The disclosures of each and every patent, patent application, and publication cited herein are hereby incorporated herein by reference in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method of treating a human subject that has been or will be exposed to radiation comprising administering to the human subject a pharmaceutical composition comprising a therapeutically effective amount of a compound of formula I, a compound of formula II, or a pharmaceutically acceptable salt thereof, or a combination thereof

I

II wherein R is —P(O)(OH)$_2$ or —P(O)(OR$_1$)(OR$_2$);
R$_1$ is H, —C$_{1-26}$alkyl, aryl, —C$_{1-6}$alkC(O)O—C$_{1-26}$alkyl, —C$_1$alkOC(O)C$_{1-26}$alkyl, or —C$_1$alkOC(O)OC$_{1-26}$alkyl; and
R$_2$ is —C$_{1-26}$alkyl, aryl, C$_{1-6}$alkC(O)O—C$_{1-26}$alkyl, —C$_1$alkOC (O)C$_{1-26}$alkyl, or —C$_1$alkOC(O)OC$_{1-26}$alkyl;
R$_3$ is H, —C(O)—Z—N(R$_4$)(R$_5$), —C(O)Z—C(O)—OH, or —C(O)—NH—Y—CH$_2$—OC(O)—Z—C(O)—OH; Z is —C$_{1-6}$alk; Y is arylene; R$_4$ is H or —C$_{1-6}$alkyl; R$_5$ is H or —C$_{1-6}$alkyl; or R$_4$ and R$_5$, together with the nitrogen to which they are attached, form a heterocycloalkyl;
or a pharmaceutically acceptable salt thereof.

2. The method of claim 1, wherein R is —P(O)(OH)$_2$.
3. The method of claim 1, wherein R is —P(O)(OR$_1$)(OR$_2$).
4. The method of claim 3, wherein R$_1$ is H.
5. The method of claim 3, wherein R$_1$ is —C$_{1-26}$alkyl.
6. The method of claim 3, wherein R$_1$ is aryl.
7. The method of claim 3, wherein R$_1$ is —C$_{1-6}$alkC(O)O—C$_{1-26}$alkyl.
8. The method of claim 3, wherein R$_1$ is —C$_1$alkOC(O)C$_{1-26}$alkyl.

9. The method of claim 3, wherein $R_1$ is —$C_1$alkOC(O)O$C_{1-26}$alkyl.

10. The method of claim 4, wherein $R_2$ is —$C_{1-26}$alkyl or aryl.

11. The method of claim 4, wherein $R_2$ is —$C_{1-6}$alkC(O)O—$C_{1-26}$alkyl.

12. The method of claim 4, wherein $R_2$ is —$C_1$alkOC(O)$C_{1-26}$alkyl.

13. The method of claim 4, wherein $R_2$ is —$C_1$alkOC(O)O$C_{1-26}$alkyl.

14. The method of claim 1, wherein the compound of formula I, and/or formula II is in the form of a pharmaceutically acceptable salt.

15. The method of claim 1, wherein the human subject is administered a pharmaceutical composition comprising a compound of formula I or a pharmaceutically acceptable salt thereof.

16. The method of claim 1, wherein the human subject is administered a pharmaceutical composition comprising a compound of formula II or a pharmaceutically acceptable salt thereof.

17. The method of claim 1, wherein the human subject has been or will be exposed to a radiation dose of between 0.3 Gy and 50 Gy.

18. The method of claim 1, wherein the human subject has been or will be exposed to a radiation dose of at least 0.7 Gy.

19. The method of claim 1, wherein the human subject has been or will be exposed to a radiation dose of at least 6 Gy, at least 10 Gy, or at least 50 Gy.

20. The method of claim 1, wherein the radiation is X-ray radiation, gamma ray radiation, neutron radiation, or a combination thereof.

21. The method of claim 1, wherein the radiation exposure is chemoradiation exposure.

22. The method of claim 1, wherein the radiation exposure is nuclear power plant leakage exposure.

23. The method of claim 1, wherein the radiation exposure is nuclear weapon exposure.

24. The method of claim 1, wherein the pharmaceutical composition is administered to the human subject 24 hours or less after the human subject has been exposed to the radiation.

25. The method of claim 1, wherein the therapeutically effective amount is 1 mg/kg to about 30 mg/kg of the compound of formula I, the compound of formula II, or a pharmaceutically acceptable salt thereof, or a combination thereof.

26. The method of claim 1, wherein the pharmaceutical composition is administered to the human subject prior to the human subject being exposed to the radiation.

27. The method of claim 1, wherein the pharmaceutical composition is administered intravenously, subcutaneously, intramuscularly, intraosseously, or transdermally.

28. The method of claim 1, wherein the pharmaceutical composition comprises the compound of formula I, the compound of formula II, or a pharmaceutically acceptable salt thereof, or a combination thereof, mannitol, a polysorbate, a povidone, an optional pH adjustor, and water.

29. The method of claim 1, wherein the treatment lowers the mortality of the human subject as a result of the radiation exposure, as compared to a control human subject that did not receive the treatment.

30. The method of claim 1, wherein the treatment improves at least one hematological parameter of the human subject, as compared to a control human subject that did not receive the treatment.

31. The method of claim 1, wherein the treatment is effective for treating hematopoietic syndrome occurring in the human subject as a result of the radiation exposure.

32. The method of claim 1, wherein the treatment is effective for treating gastrointestinal syndrome occurring in the human subject as a result of the radiation exposure.

33. The method of claim 1, wherein the treatment is effective for treating cardiovascular syndrome occurring in the human subject as a result of the radiation exposure.

34. The method of claim 1, wherein the treatment is effective for treating central nervous system syndrome occurring in the human subject as a result of the radiation exposure.

35. The method of claim 1, wherein the treatment is effective for treating anorexia, nausea, vomiting, cramps, or diarrhea occurring in the human subject as a result of the radiation exposure.

36. The method of claim 1, wherein the treatment is effective for treating cognitive changes or behavior changes occurring in the human subject as a result of the radiation exposure.

37. The method of claim 1, wherein the pharmaceutical composition comprises a ditromethamine salt of Formula I-A:

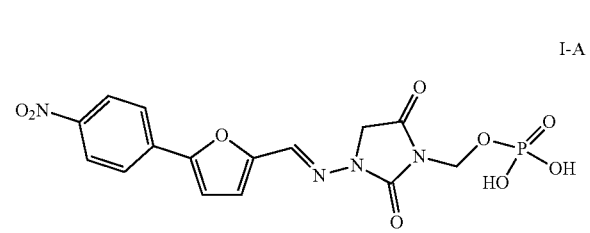 [SMILES: O=C1CN(/N=C/c2ccc(-c3ccc([N+](=O)[O-])cc3)o2)C(=O)N1COP(=O)(O)O]

I-A

* * * * *